(12) United States Patent
Li et al.

(10) Patent No.: US 9,138,234 B2
(45) Date of Patent: Sep. 22, 2015

(54) CLIP APPARATUS FOR LIGATURE OF LIVING TISSUE

(71) Applicant: ANREI MEDICAL (HZ) CO., LTD., Hangzhou (CN)

(72) Inventors: Changqing Li, Bloomington, IN (US); Baiming Shi, Hangzhou (CN)

(73) Assignee: ANREI MEDICAL (HZ) CO., LTD., Hangzhou (CN)

( * ) Notice: Subject to any disclaimer, the term of this patent is extended or adjusted under 35 U.S.C. 154(b) by 385 days.

(21) Appl. No.: 13/675,457

(22) Filed: Nov. 13, 2012

(65) Prior Publication Data
US 2013/0123818 A1 May 16, 2013

Related U.S. Application Data

(60) Provisional application No. 61/559,374, filed on Nov. 14, 2011.

(51) Int. Cl.
*A61B 17/08* (2006.01)
*A61B 17/122* (2006.01)

(52) U.S. Cl.
CPC ............ *A61B 17/122* (2013.01); *A61B 17/1222* (2013.01); *A61B 17/1227* (2013.01)

(58) Field of Classification Search
CPC .. A61B 17/128; A61B 17/1285; A61B 17/12; A61B 2017/12004; A61B 17/122; A61B 17/1227; A61B 17/1222
USPC .......... 606/142, 143, 157, 158, 139, 151, 219
See application file for complete search history.

(56) References Cited

U.S. PATENT DOCUMENTS

| | | | | |
|---|---|---|---|---|
| 5,407,243 A | * | 4/1995 | Riemann | 294/100 |
| 7,727,247 B2 | * | 6/2010 | Kimura et al. | 606/157 |
| 8,070,760 B2 | * | 12/2011 | Fujita | 606/142 |
| 2003/0069592 A1 | * | 4/2003 | Adams et al. | 606/142 |
| 2006/0155308 A1 | * | 7/2006 | Griego | 606/142 |
| 2006/0224165 A1 | * | 10/2006 | Surti et al. | 606/142 |
| 2008/0255427 A1 | * | 10/2008 | Satake et al. | 600/204 |
| 2009/0326558 A1 | * | 12/2009 | Cui et al. | 606/143 |
| 2010/0152753 A1 | * | 6/2010 | Menn et al. | 606/158 |
| 2011/0054498 A1 | * | 3/2011 | Monassevitch et al. | 606/142 |

FOREIGN PATENT DOCUMENTS

| | | | | |
|---|---|---|---|---|
| EP | 1829489 | | 9/2007 | |
| EP | 1829489 A1 | * | 9/2007 | ........... A61B 17/122 |
| EP | 1882451 | | 1/2008 | |
| EP | 1882451 A2 | * | 1/2008 | |
| EP | 1884209 | | 2/2008 | |
| EP | 1884209 A2 | * | 2/2008 | ........... A61B 17/128 |

OTHER PUBLICATIONS

EPO Search Report for Application No. EP12192409.6.

* cited by examiner

*Primary Examiner* — Todd Manahan
*Assistant Examiner* — Charles Wei
(74) *Attorney, Agent, or Firm* — Preti Flaherty Beliveau & Pachios LLP

(57) ABSTRACT

A clip apparatus for ligature of living tissue is provided. The clip apparatus includes a clip that can be opened and closed multiple times prior to locking in a closed position on the tissue.

3 Claims, 24 Drawing Sheets

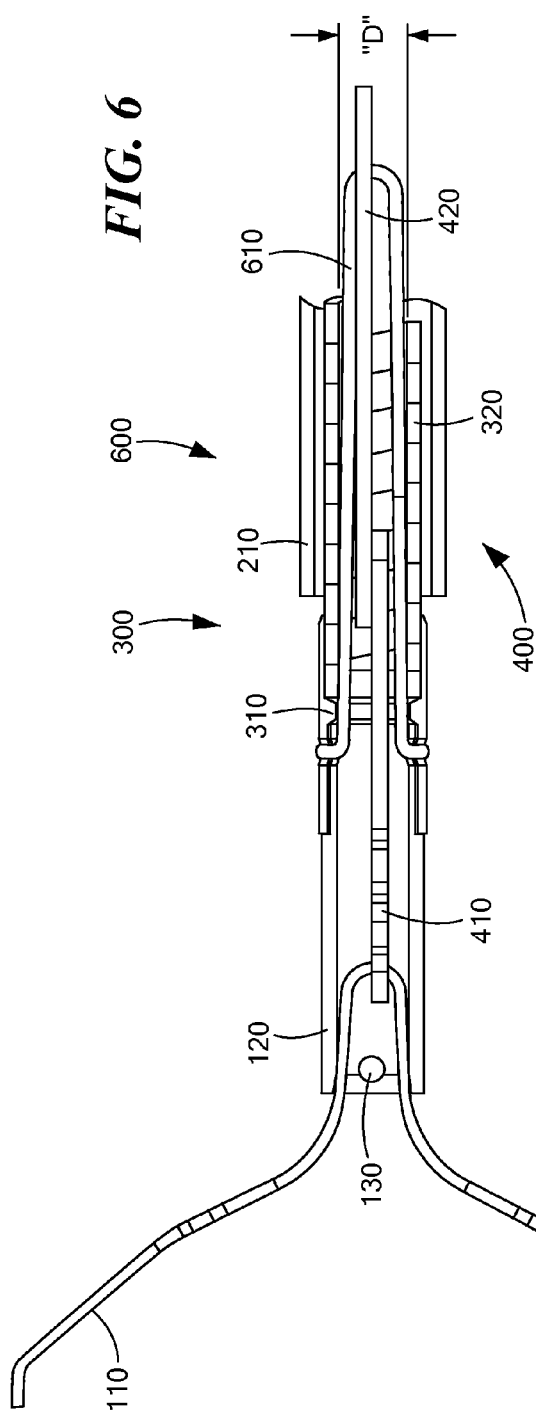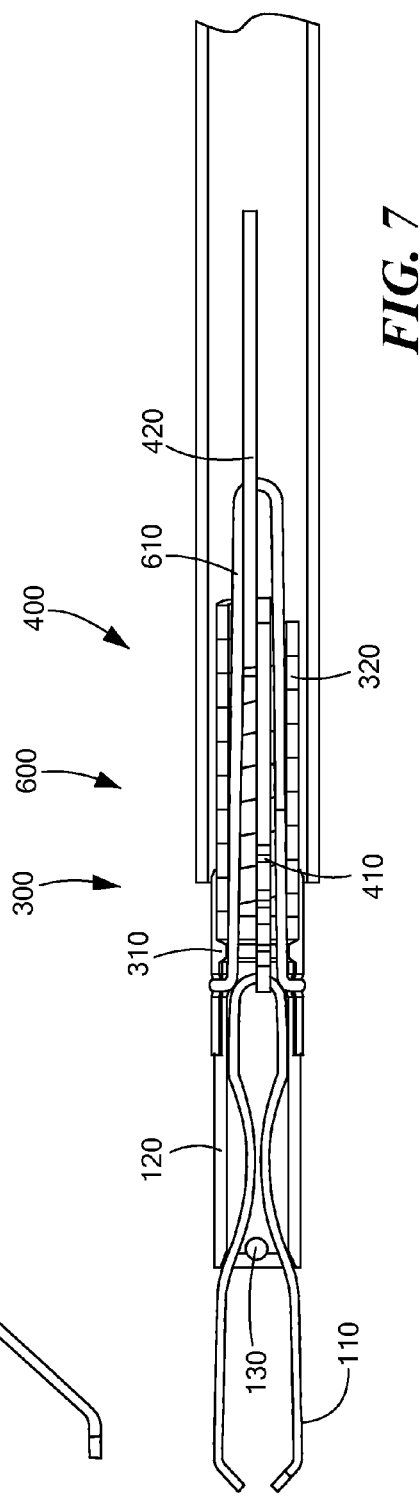

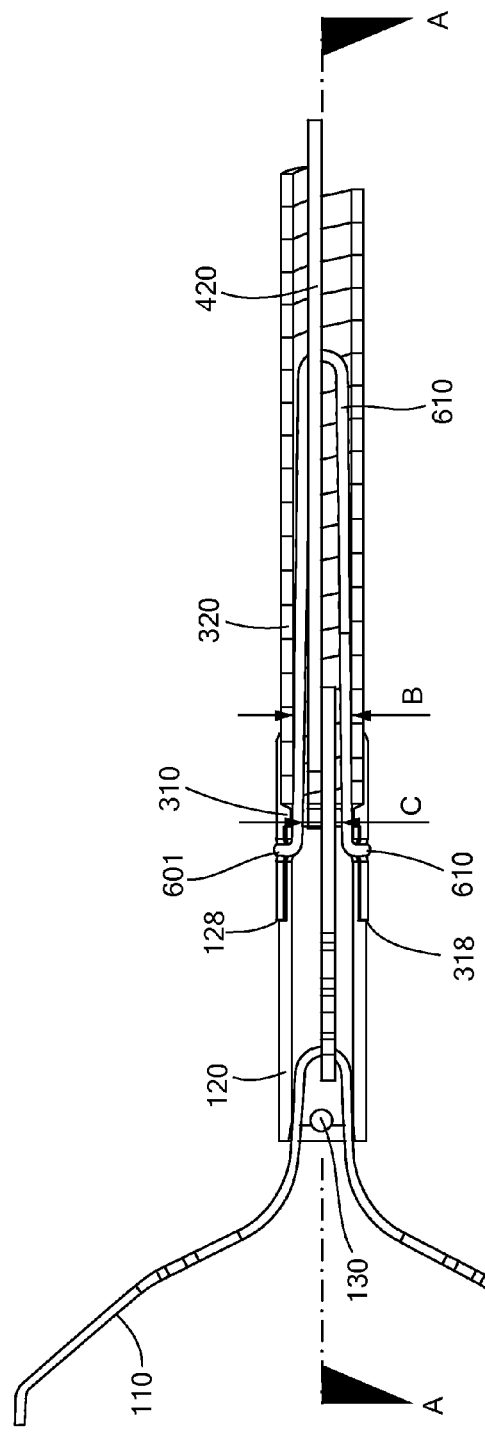
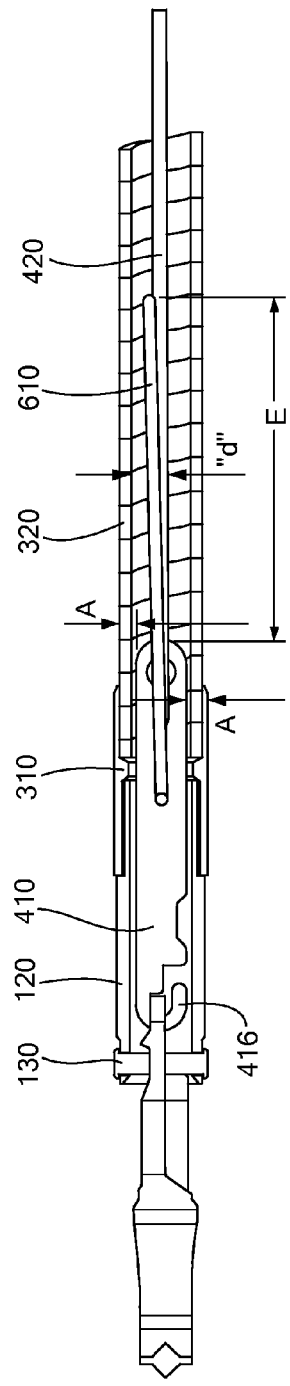
FIG. 8A
FIG. 8B

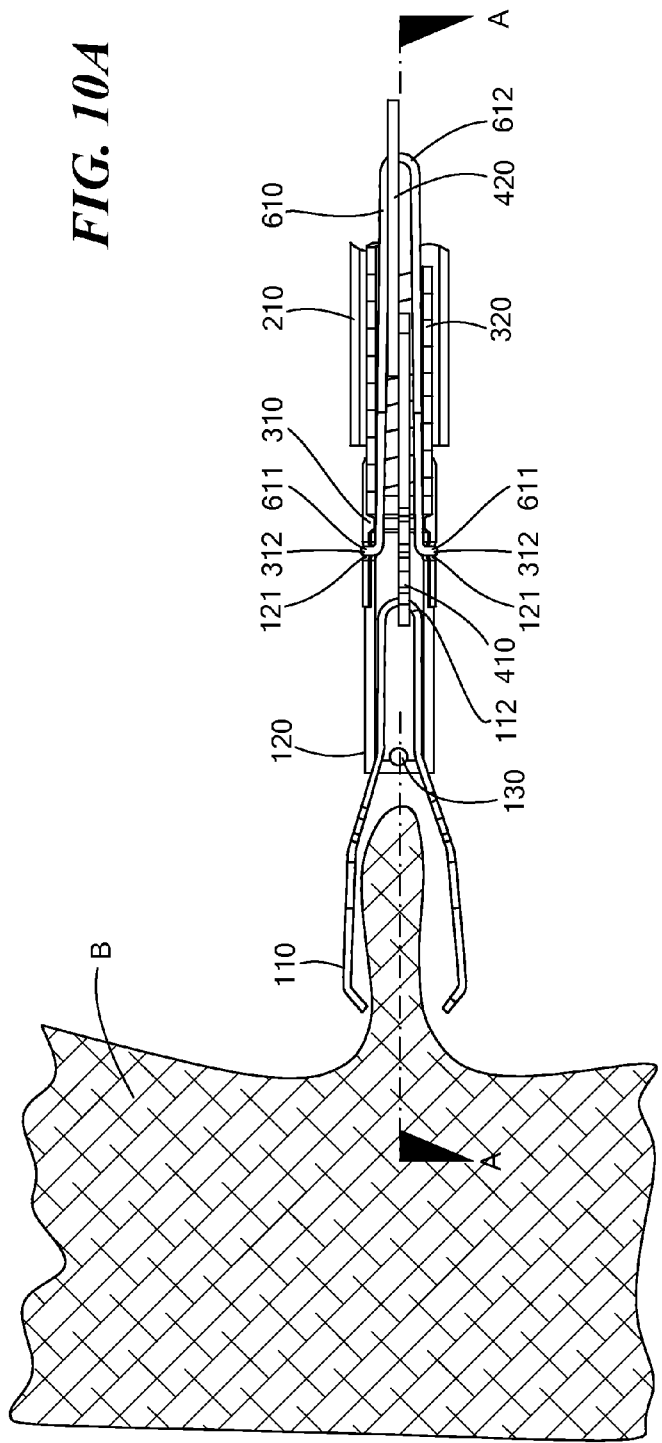

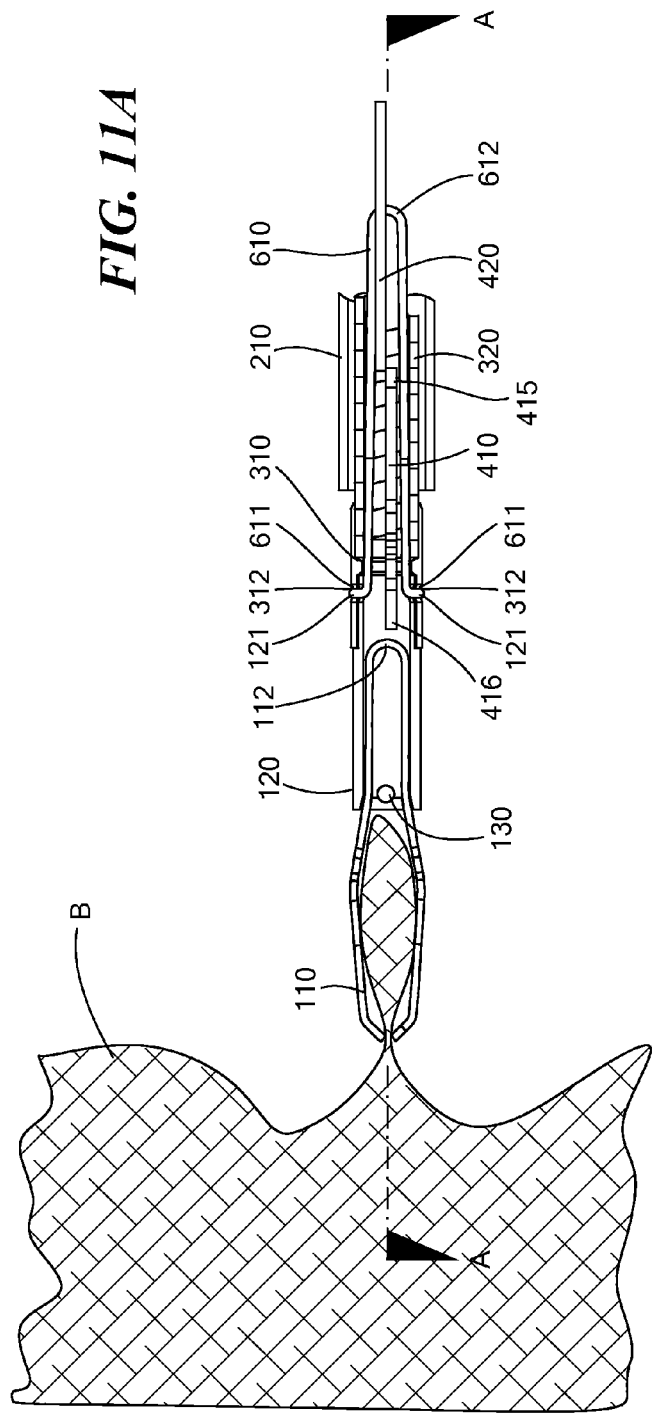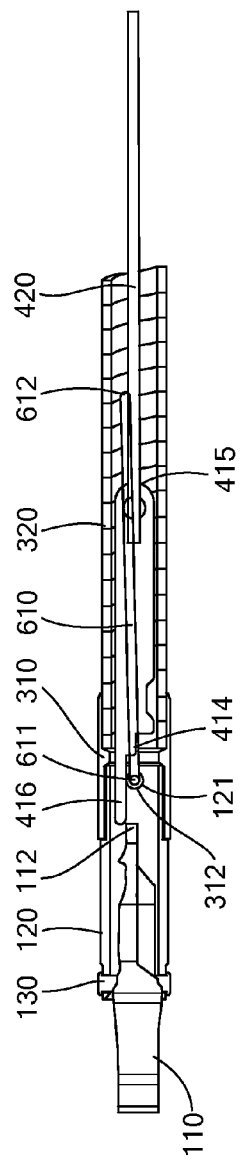
FIG. 11A
FIG. 11B

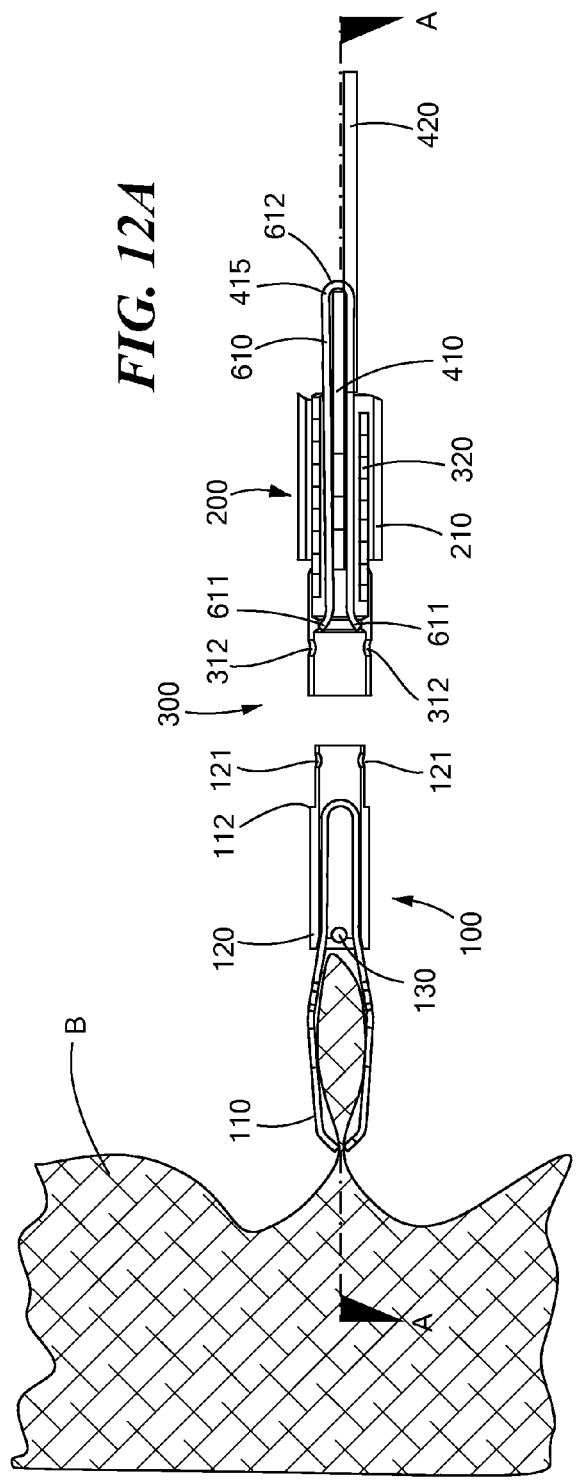
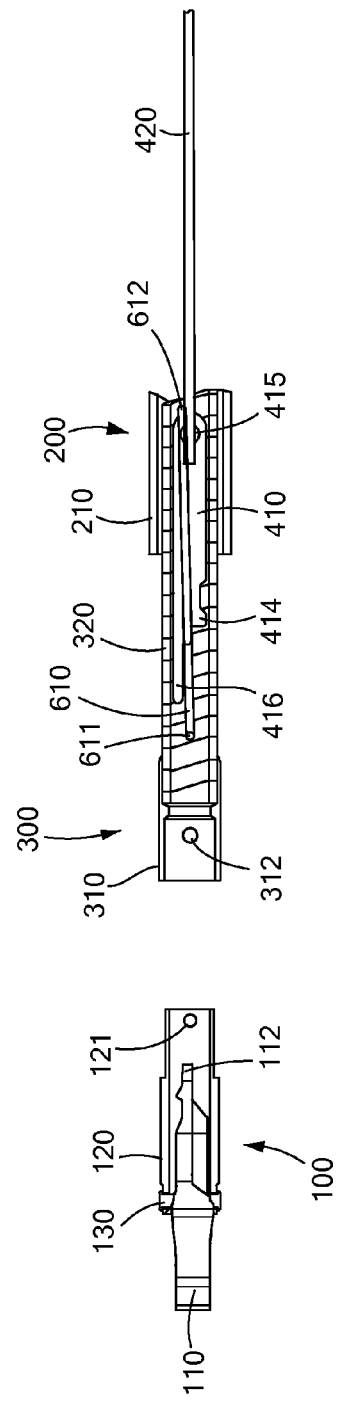
FIG. 12A
FIG. 12B

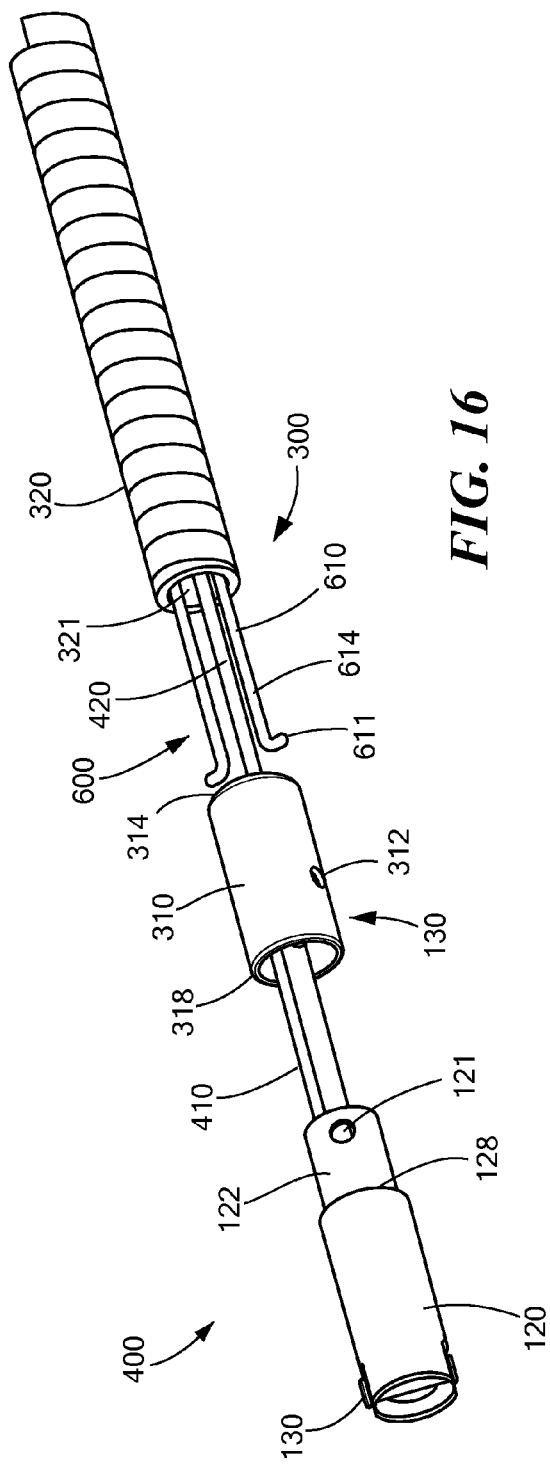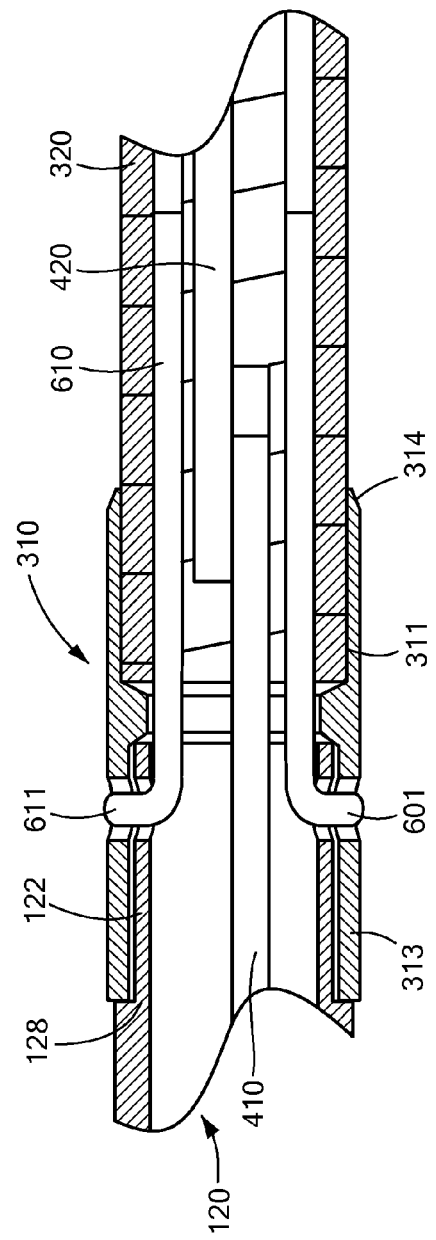

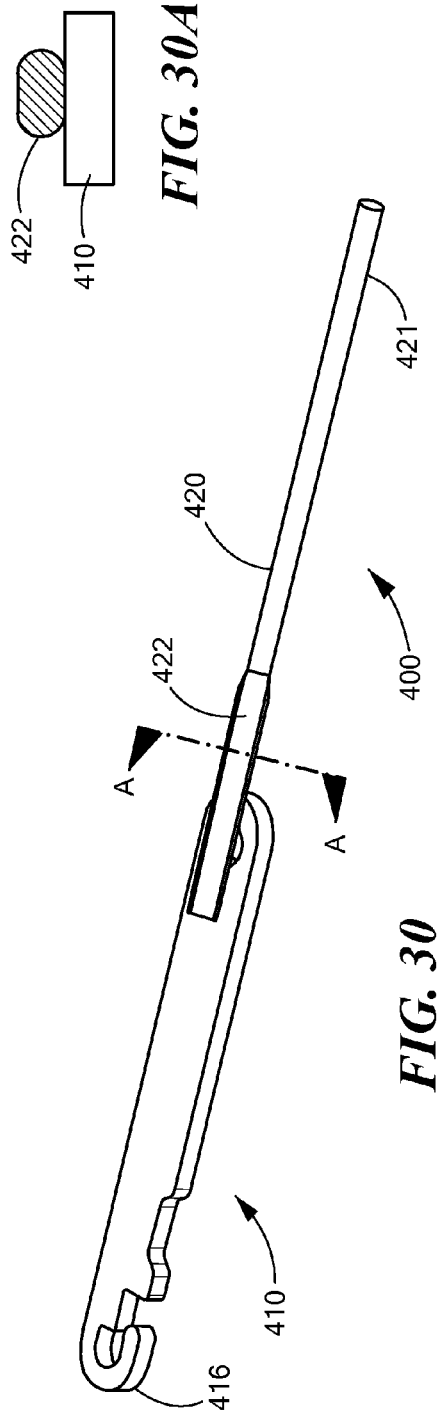
FIG. 30
FIG. 30A
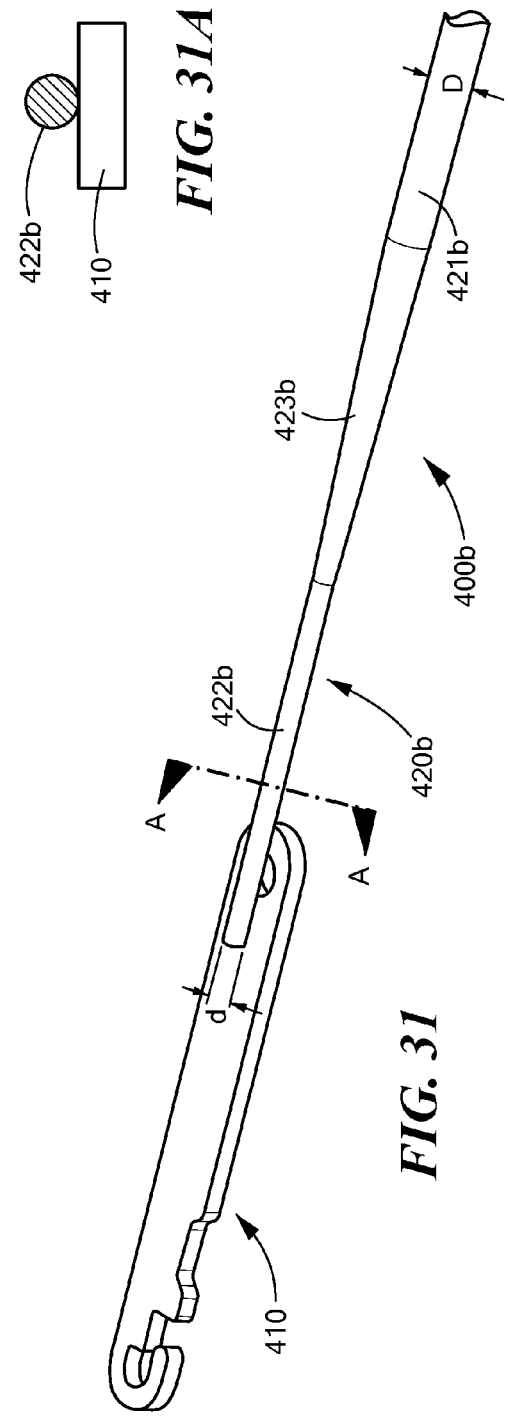
FIG. 31
FIG. 31A

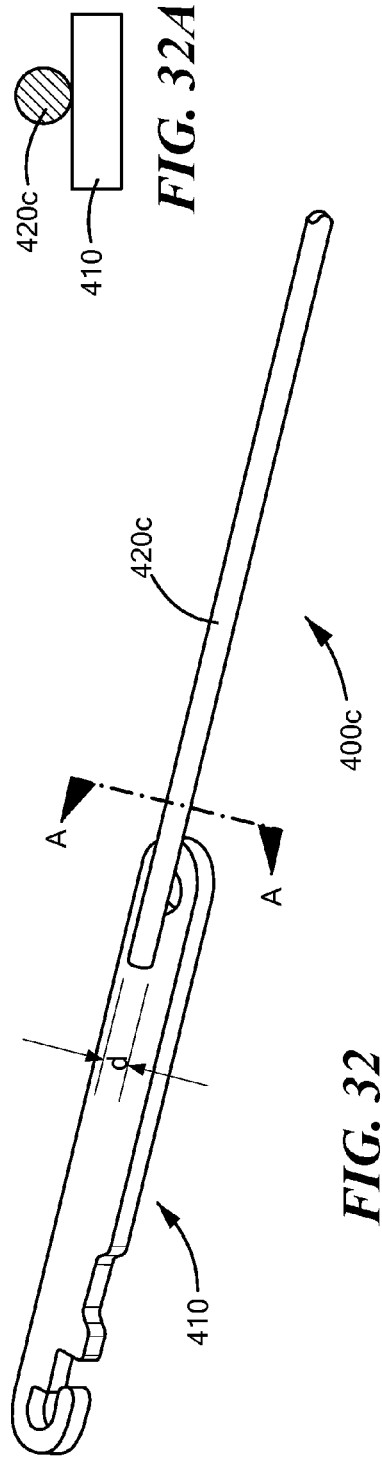
FIG. 32
FIG. 32A
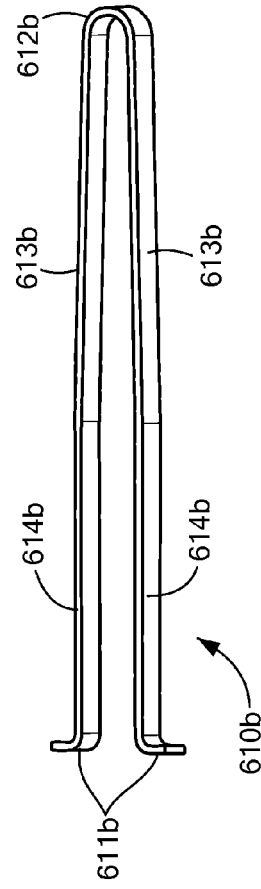
FIG. 33
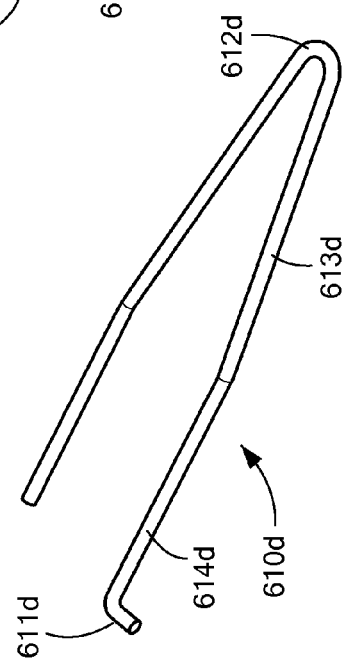
FIG. 34

CLIP APPARATUS FOR LIGATURE OF LIVING TISSUE

CROSS REFERENCE TO RELATED APPLICATIONS

This application claims the benefit under 35 U.S.C. 119(e) of U.S. Provisional Patent Application No. 61/559,374, filed on Nov. 14, 2011, the disclosure of which is incorporated by reference herein.

STATEMENT REGARDING FEDERALLY SPONSORED RESEARCH OR DEVELOPMENT

N/A

BACKGROUND OF THE INVENTION

Medical doctors are able to perform various procedures within a patient's gastrointestinal (GI) tract using a flexible endoscopic device. Bleeding from blood vessels or perforations of the GI tract can occur. Sometimes, such occurrences constitute a medical emergency, in which bleeding must be stopped rapidly. Endoscopic clips usable with a flexible endoscopic device are known for clamping blood vessels or a section of tissue to stop bleeding or close perforations.

SUMMARY OF THE INVENTION

A clip apparatus for ligature of living tissue is provided that can be opened and closed multiple times before being clamped on the section of tissue. The ability to open and close a clip multiple times provides a user with more flexibility in placing a clip. The clip can be closed over a section of tissue, and the area can be washed off. The user can then see whether placement of the clip should be adjusted. If necessary, the user can open the clip and reclose it in a different position. Once the user determines that the clip has been suitably placed, the clip apparatus can be actuated to leave the locked clip in place in the body.

DESCRIPTION OF THE DRAWINGS

The invention will be more fully understood from the following detailed description taken in conjunction with the accompanying drawings. The drawings illustrate a variety of embodiments and features of the clip apparatus.

FIG. 6 is a cross sectional view of the clip apparatus with the clip unit in an open position;

FIG. 7 is a cross sectional view of the clip apparatus with the clip unit in an closed position;

FIG. 8A is a cross sectional view of the clip apparatus n an open position;

FIG. 8B is a cross sectional view along the line A-A of FIG. 8A;

FIG. 10A is a cross sectional view of the clip apparatus with the clip unit closing to grasp tissue;

FIG. 10B is a cross sectional view along line A-A of FIG. 10B;

FIG. 11A is a cross sectional view of the clip apparatus with the clip unit closed to grasp tissue;

FIG. 11B is a cross sectional view along line A-A of FIG. 11A;

FIG. 12A is a cross sectional view of the clip apparatus with the clip unit deployed;

FIG. 12B is a cross sectional view along line A-A of FIG. 12B;

FIG. 16 is an exploded isometric view illustrating an introducing mechanism, coupling mechanism, and release mechanism of the embodiment of FIGS. 4-12B;

FIG. 17 is a partial cross sectional view of the introducing mechanism, coupling mechanism, and release mechanism of FIGS. 4-12B;

FIG. 30 is an isometric view of a control wire and coupling plate;

FIG. 30A is a cross sectional view taken along line A-A of FIG. 30;

FIG. 31 is an isometric view of a further embodiment of a control wire and coupling plate;

FIG. 31A is a cross sectional view taken along line A-A of FIG. 31;

FIG. 32 is an isometric view of a still further embodiment of a control wire and coupling plate;

FIG. 32A is a cross sectional view taken along line A-A of FIG. 32;

FIG. 33 is an isometric view of a further embodiment of a spring clip;

FIG. 34 is an isometric view of a further embodiment of a spring clip;

DETAILED DESCRIPTION OF THE INVENTION

The disclosure of U.S. Provisional Patent Application No. 61/559,374, filed on Nov. 14, 2011, is incorporated by reference herein.

Figure 1:
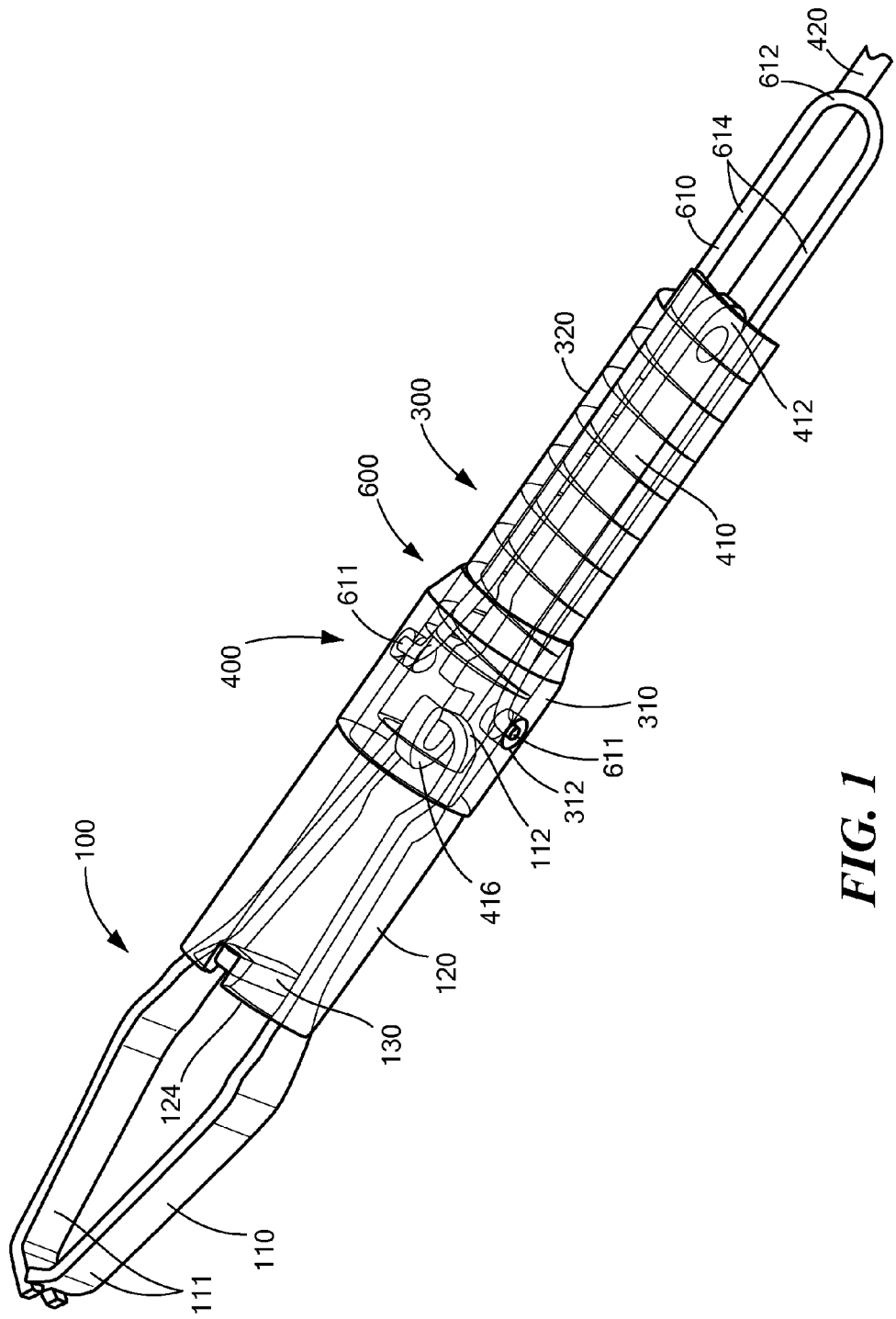
FIG. 1 is a schematic illustration of an embodiment of a clip apparatus for the ligature of living tissue in a closed position.
Figure 2:
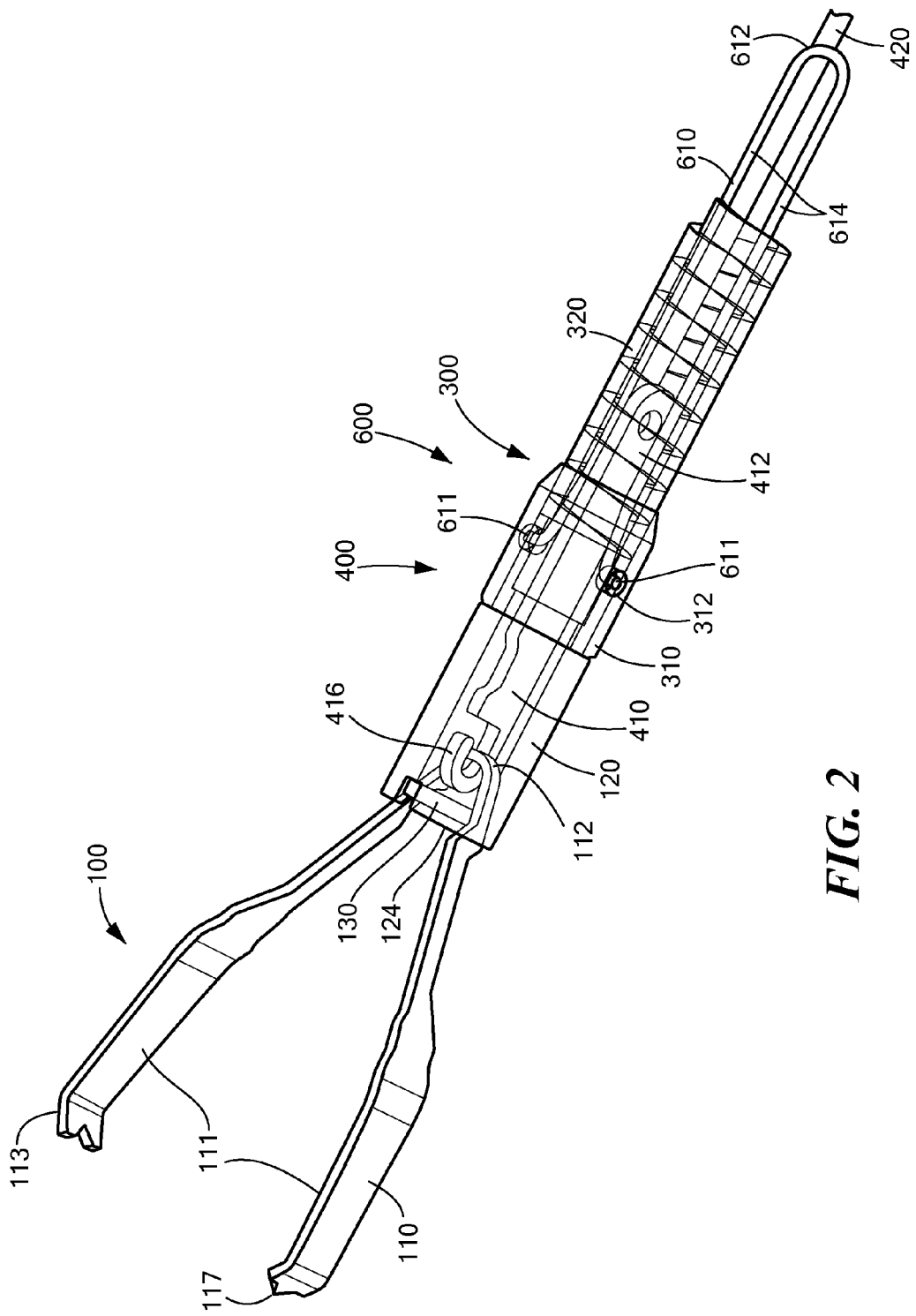
FIG. 2 is a schematic illustration of the clip apparatus in an open position.
Figure 3:
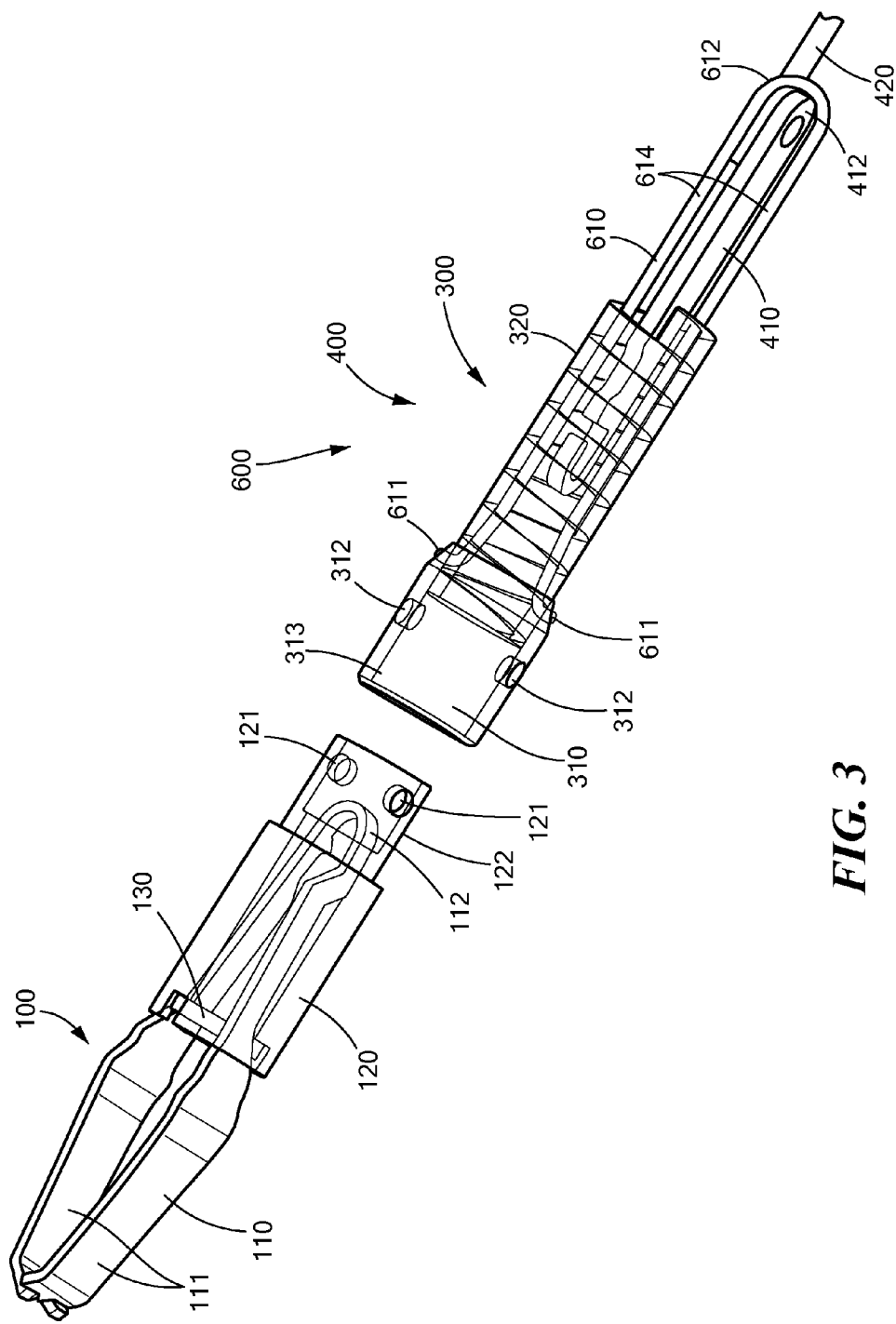
FIG. 3 is a schematic illustration of the clip apparatus in a deployed position.
Figure 4:
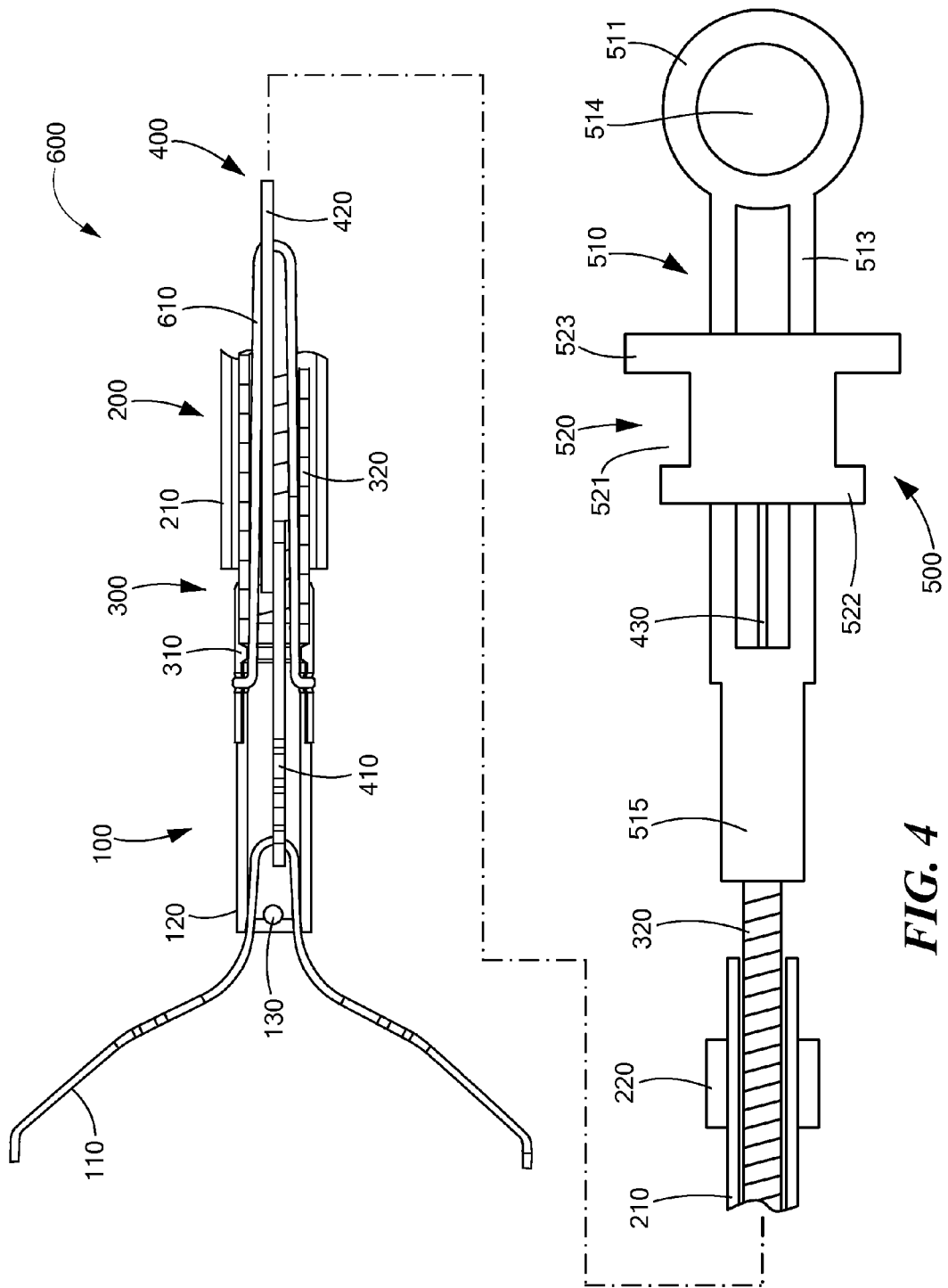
FIG. 4 is a cross sectional view of the clip apparatus also illustrating a handle operation unit.
Figure 5:
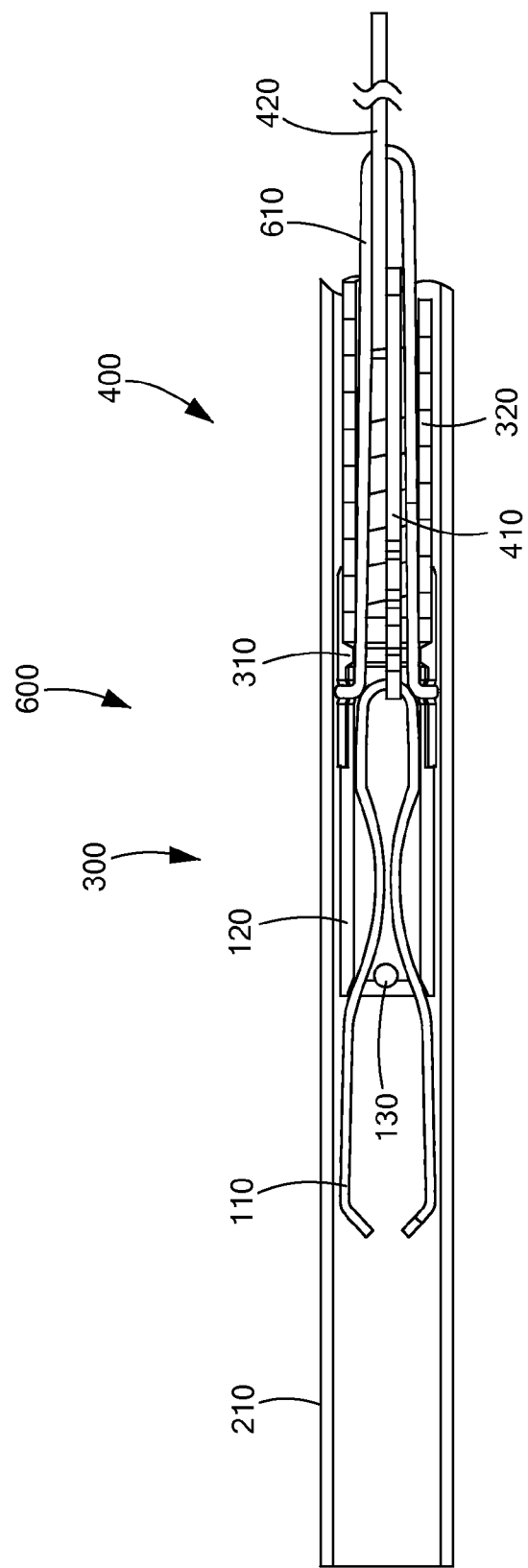
FIG. 5 is a cross sectional view of the clip apparatus within an outer sheath.
Figure 9A:
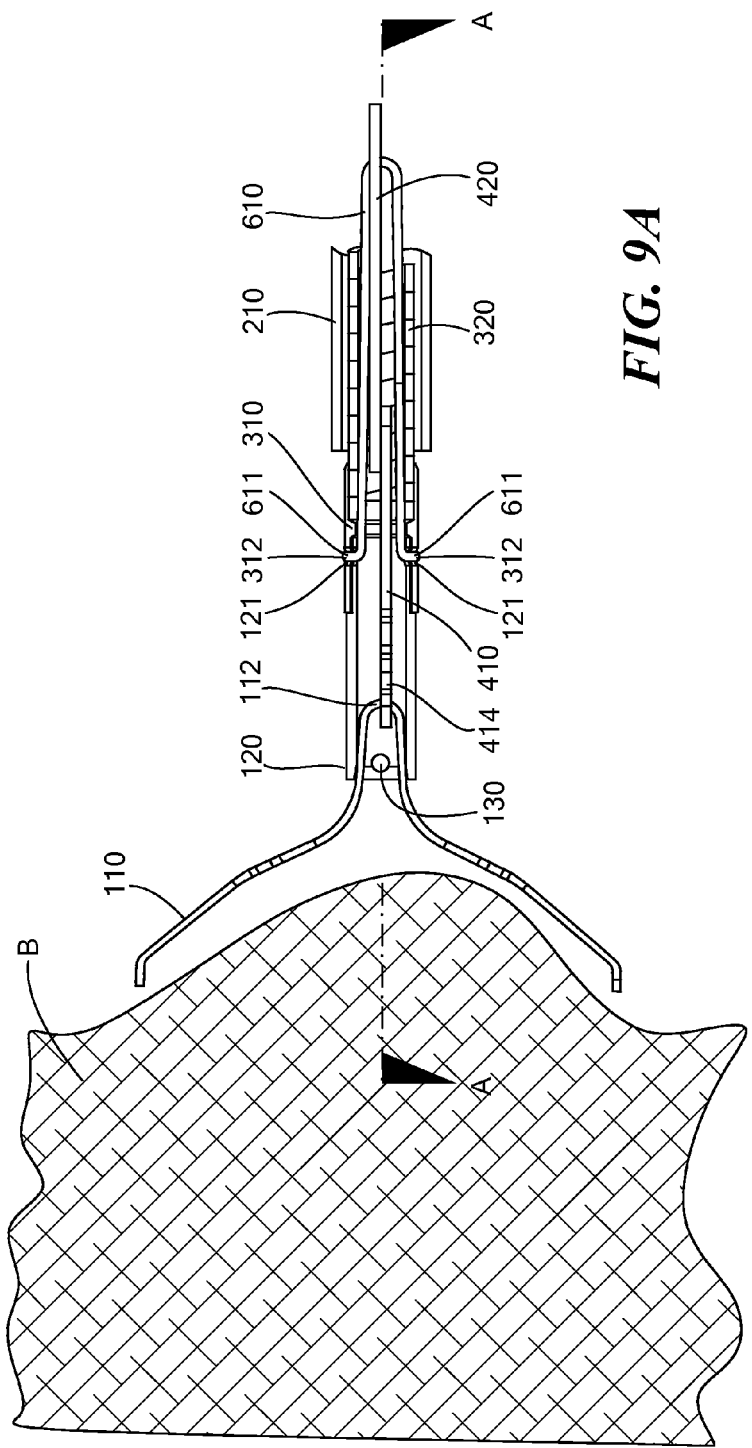
FIG. 9A is a cross sectional view of the clip apparatus beginning to grasp tissue.
Figure 13:
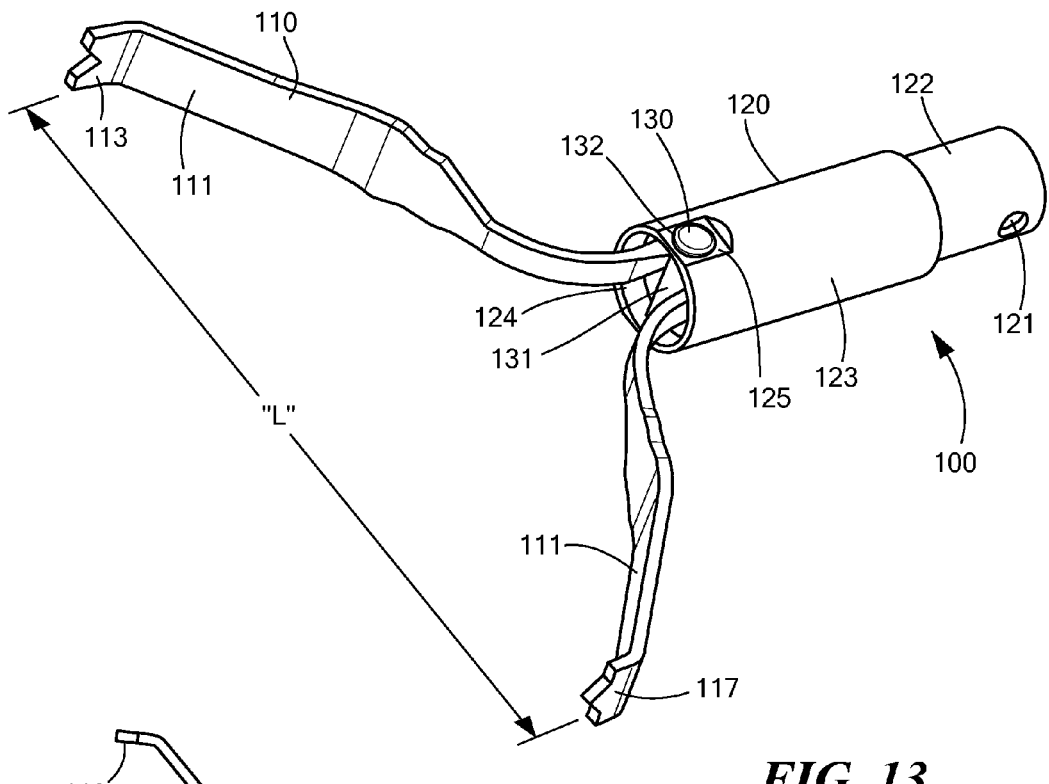
FIG. 13 is an isometric view of a clip unit of the clip apparatus of FIGS. 4-12B.
Figure 14:
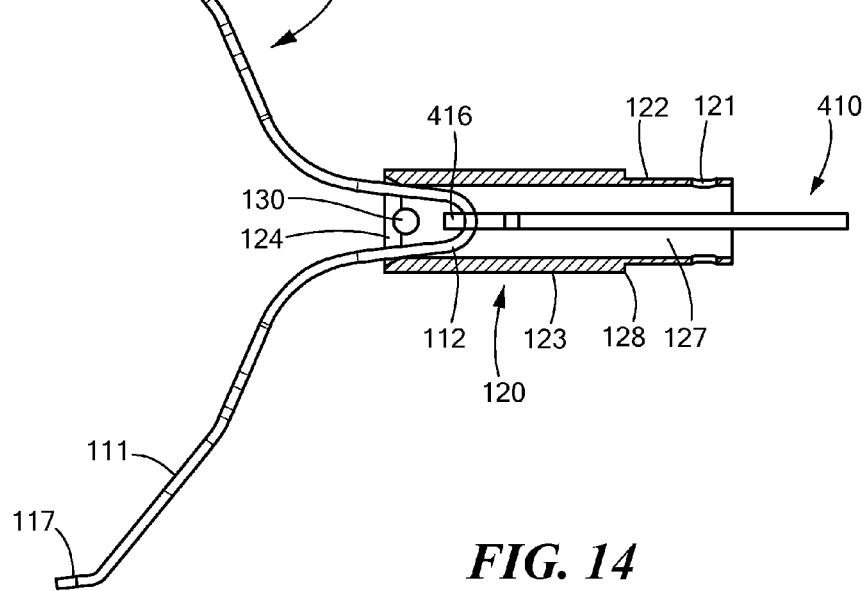
FIG. 14 is a cross-sectional view of the clip unit of FIG. 13.

One embodiment of a clip apparatus is illustrated in conjunction with FIGS. 1-4. The clip apparatus includes a clip unit 100, which includes a clip 110, a tightening ring 120 and a spacer member 130, such as a pin. The clip includes two arms 111 that are biased outwardly, as shown in FIGS. 2 and 4. See also FIGS. 13 and 14. The arms are joined at a proximal base 112, which is formed as a U-shaped bend in the embodiment shown. Each of the two arms includes a jaw end 113, 117, formed with a gripping tooth or gripping teeth. The gripping tooth or teeth can be cooperatively shaped to interlock. The clip 110 can be retracted within the tightening ring 120 to force the arms together, thereby allowing the jaw ends to close together for grasping tissue. See FIGS. 1 and 7. See also FIGS. 10A, 10B, 11A, and 11B. The spacer member 130 extends radially across a distal opening 124 of the tightening ring 120. The spacer member 130 forces the arms apart as the clip is extended outside of the tightening ring. See FIGS. 2 and 4. See also FIGS. 6, 8A, and 9A. The arms can also be formed from a springy metal to aid in biasing them open. The opening 124 can also be chamfered on the inside surface. The spacer member can be fastened to the tightening ring in any suitable manner, such as, without limitation, by a mechanical mechanism, welding, or adhesive.

Figure 9B:
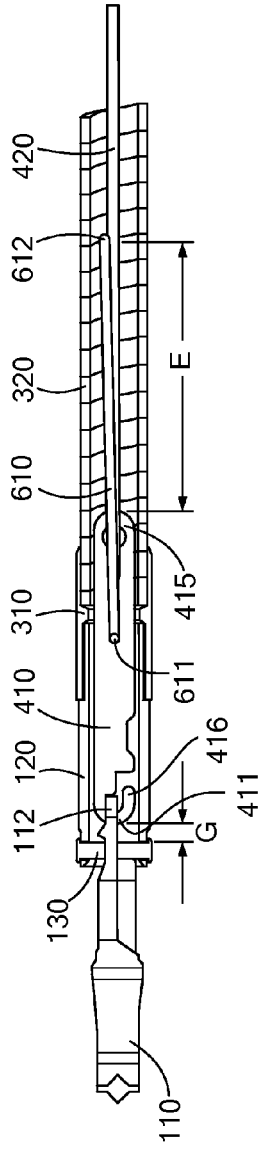
FIG. 9B is a cross sectional view along line A-A of FIG. 9A.

The clip unit 100 is attached to a coupling mechanism 400. The coupling mechanism includes a coupling plate 410 having a hook 416 at the distal end. See also FIGS. 8B, 9B, and 10B. The hook attaches to the proximal base 112 of the clip 110. The coupling mechanism includes a control wire 420 that is attached to a proximal end 412 of the coupling plate 410. The control wire is sufficiently stiff so that it can exert tensile and compressive forces via the coupling plate 410 on the clip unit 100 to cause the clip unit to extend or retract. The hook 416 on the coupling plate 410 is bendable or frangible so that it is able to detach from the base 112 of the clip 110 upon exertion of a sufficiently large tensile force via the control wire 420, described further below, when it is desired to lock the clip closed and leave it in place in the body. See FIGS. 11A, 11B, 12A, 12B.

The control wire 420 may be formed, for example, from a single wire or a plurality of wires twisted together. Any suitable material, for example, a metal such as stainless steel, may be used for the control wire. The coupling plate 410 may be formed of any suitable material, for example, a metal such as stainless steel. It may be formed from a single material, a composite material, as a single unitary piece, or as a lamination.

The control wire 420 extends through an outer sheath 200 to a handle operation unit 500. See FIG. 4. The outer sheath includes a tube 210 that houses and protects the clip unit 100 during insertion and maintains the clip 110 in a closed position as it is passed through an endoscope channel. A handle element 220 may optionally be provided on the tube of the outer sheath, if desired.

The control wire 420 also extends through an introducing mechanism 300 including an inner sheath or spring tube 320 coaxially disposed within the outer sheath 200. See FIG. 4. The spring tube 320 is attached at a distal end to a coupling ring 310. The spring tube is attached at a proximal end to a handle operation unit 500. Both the outer sheath 200 and the spring tube 320 are flexible so that the device can bend. The spring tube may be formed from any suitable material, for example, from twisted metal plates or twisted metal wire.

The handle operation unit 500 includes a handle 510 and a slider 520 mounted for linear reciprocating movement with respect to the handle. See FIG. 4. A proximal end of the spring tube 320 is attached to a distal end 515 of the handle operation unit 500, and a proximal end 430 of the control wire 420 is attached to the slider 520. The handle includes a thumb ring 511 with a hole 514 sized to receive a user's thumb. The slider includes finger grips 521 defined by flanges or shoulders 522, 523 shaped to receive fingers of a user's hand. When the user grasps the handle operation unit through the thumb hole 514 and the finger grips 521, the user can reciprocate the slider 520 linearly along tracks or rails 513 of the handle, which in turn moves the control wire in a distal or proximal direction. In this manner, the user can exert tensile and compressive forces via the coupling plate on the clip unit to cause the clip unit to extend or retract. The handle operation unit 500 can also include a rotatable component (such as the handle 510 or slider 520) to rotate the clip unit if necessary.

Figure 15A:
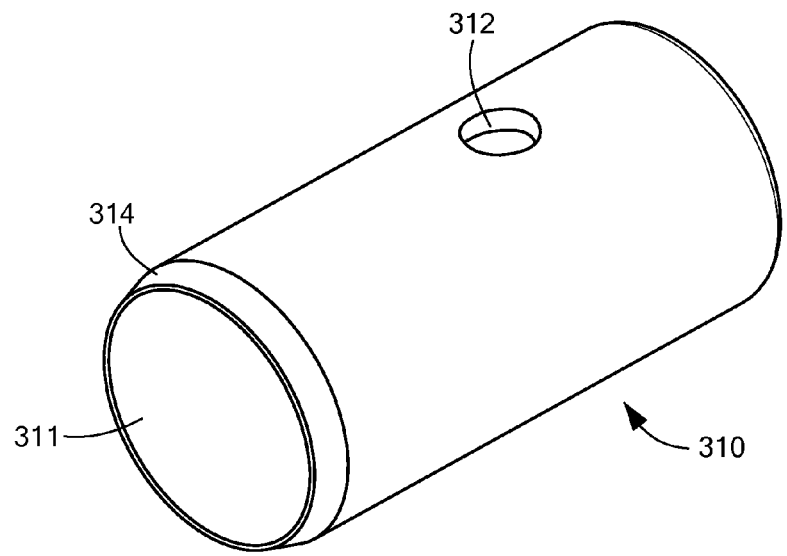
FIG. 15A is an isometric view of the coupling ring.
Figure 15B:
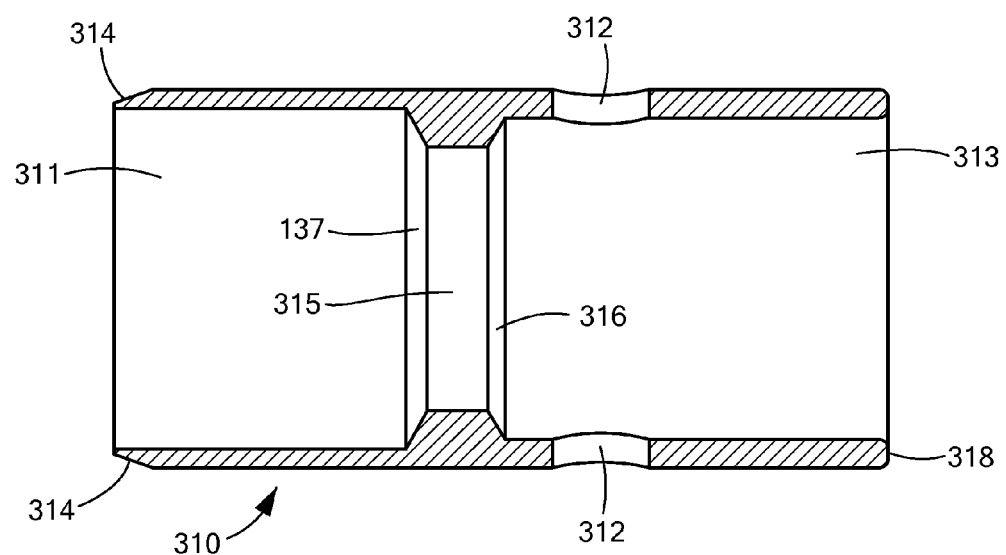
FIG. 15B is a cross sectional view of the coupling ring of FIG. 15A.

As noted above, the distal end of the spring tube 320 is attached to the coupling ring 310. The coupling ring is cylindrical and includes a pair of opposed openings 312. See also FIGS. 15A, 15B. The tightening ring 120 is also cylindrical and includes a proximal section 122 of reduced outer diameter that fits within the inner diameter of a distal section 313 of the coupling ring 310. See also FIGS. 16 and 17. The tightening ring 120 also includes a pair of opposed openings 121 on the proximal section that are alignable with the opposed openings 312 of the coupling ring 310.

Figure 18:
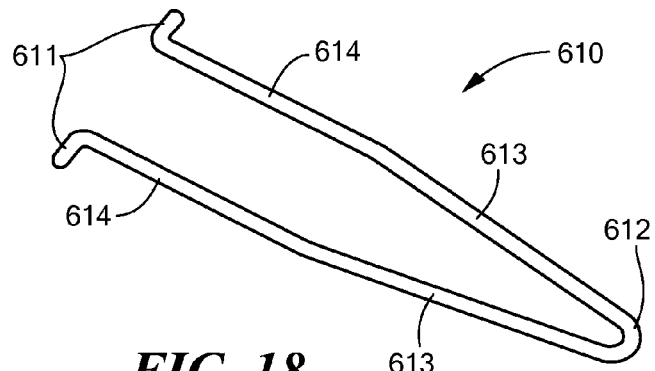
FIG. 18 is an isometric view of the spring clip of FIGS. 4-12B.

A release mechanism 600 includes a spring pin 610 provided to releasably couple the coupling ring 310 and the tightening ring 120 when the openings 312, 121 are aligned. The spring pin 610 is generally U-shaped and includes a proximal base 612 and two arms 314. See FIG. 18. The distal tips 611 of each of the arms 614 face outwardly, for example, by bending the tips of the arms. The tips fit within the opposed openings 312, 121 of both the tightening ring 120 and the coupling ring 310.

Operation of the clip apparatus can be described with reference to FIGS. 5-12B. In operation, the clip unit 100, attached to the introducing mechanism 300, is inserted through the outer sheath 200 to the general location in the body where the clip 110 is to be deployed. The clip arms 111 are held closed while the clip unit is within the outer sheath. See FIG. 5. The clip unit 100 is pushed entirely through the outer sheath until it exits the distal end, whereupon the arms of the clip spring open. See FIGS. 6, 8A, 8B.

The user than manipulates the control wire 420 via the slider 520 on the handle 510 to move the clip 110 proximally or distally. As the clip reciprocates, it translates linearly with respect to the tightening ring 120. Pulling the clip in a proximal direction causes the clip to retract within the tightening ring, which forces the spring arms 111 closed. See FIG. 7. Pushing the clip in a distal direction causes the clip to extend outside of the tightening ring, allowing the spring arms to open. In this manner, the user can open and close the arms until the clip is satisfactorily positioned. See FIGS. 9A, 9B, 10A, and 10B. The user can irrigate the area to get a clear view of where the clip is attached to the tissue. The clip can be reopened and reattached to the tissue as often as necessary.

When the clip 110 is satisfactorily positioned on a section of tissue, the user pulls on the control wire 420 with a greater force, which causes the hook 416 on the coupling plate 410 to bend or break and detach from the proximal base 112 of the clip 110. See FIGS. 11A, 11B. Continued tensile force on the control wire causes the coupling plate to withdraw in a proximal direction. As the coupling plate withdraws further, the proximal end 412 of the coupling plate abuts the proximal base 612 of the spring pin 610. The spring pin is thereby moved in the proximal direction. As the spring pin moves, the distal tips 611 slip out of the aligned openings 121, 312 in the tightening ring 120 and the coupling ring 310. The tightening ring and the coupling ring thus become uncoupled. See FIGS. 12A, 12B.

Continued tensile force on the control wire 420 pulls the coupling plate 410, the spring pin 610, and the coupling ring 310 away from the clip unit 110. The tightening ring 120 remains in place over the clip arms 111, locking the arms in the closed position over the tissue. The rest of the apparatus can be withdrawn from the body.

The clip unit 100 is made from a suitable medical grade material, such as a stainless steel or a shape memory alloy. After a period of time, the clamped tissues dies. The clip unit falls off and passes out of the patient's body through the GI tract.

The outer sheath 200 can be made from a suitable material, such as a polymeric resin or other engineered plastics. Examples include, but are not limited, to polytetrafluoroethylene, polyethylene, polypropylene, polyamide, fluorinated ethylene propylene, polyether block amides such as PEBAX®, or a nylon.

The other elements can be made from any suitable material, such as stainless steel.

The figures illustrate further embodiments having a variety of features and aspects. It will be appreciated the various features and aspects can be used in any of the various embodiments.

Figure 19A:
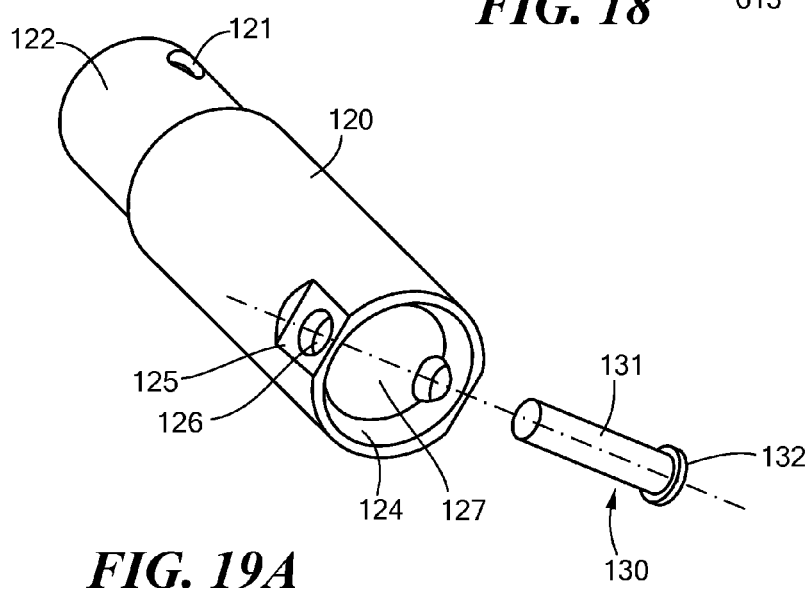
FIG. 19A is an isometric view of the spacer member of the clip unit.
Figure 19B:
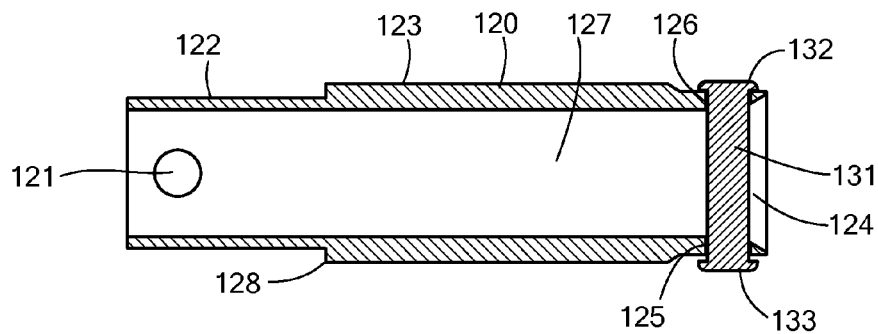
FIG. 19B is a cross sectional view of the spacer member and tightening ring.

In one embodiment, the spacer member 130 is a pin that fits through opposed apertures 126 on the tightening ring 120. See FIGS. 19A and 19B. A head 132 on one end of the body 131 of the pin fits within a recess 125 surrounding one of the apertures 126. The other end of the pin protrudes slightly through the opposed aperture 126, and during manufacture, a head 133 can be formed on the other end of the pin to retain the pin in place across the distal opening of the tightening ring.

Figure 20A:
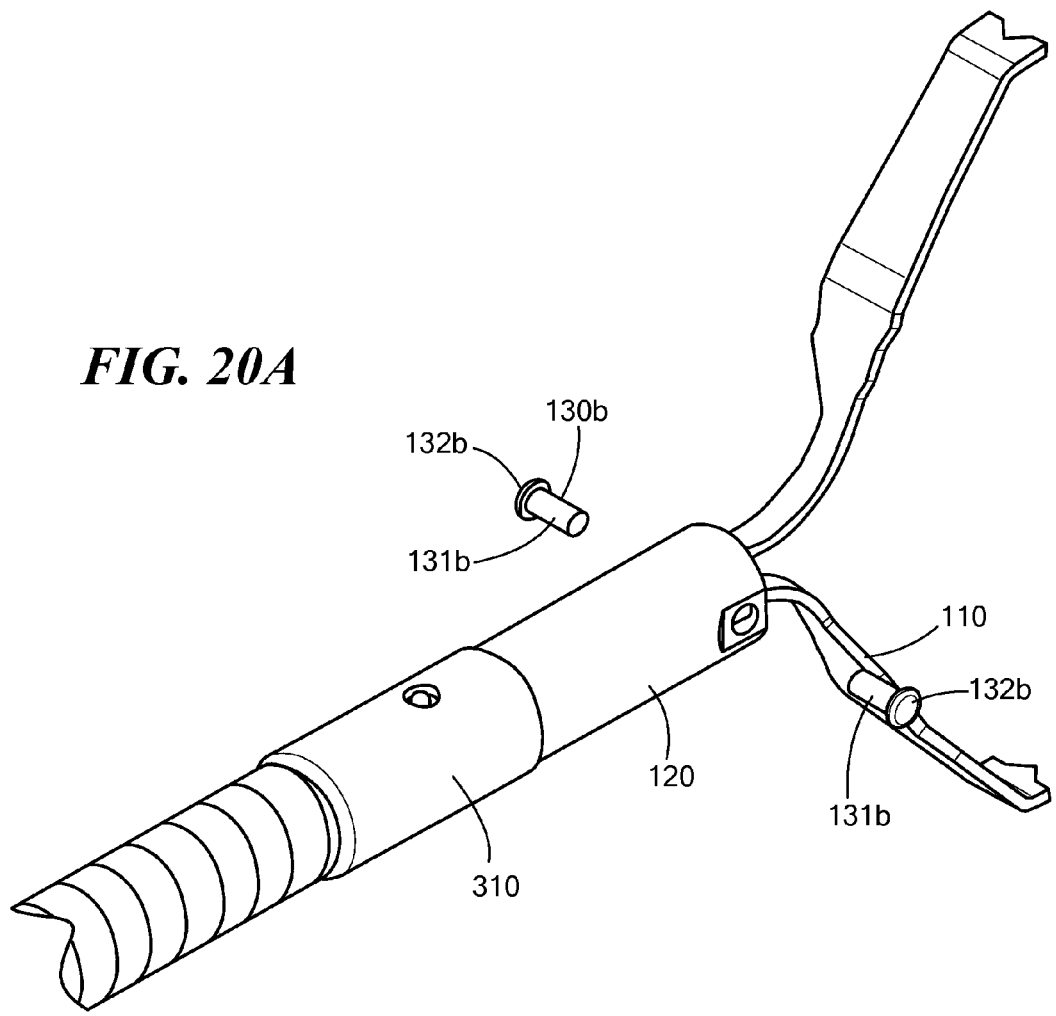
FIG. 20A is an isometric, partially exploded view of a further embodiment of a spacer member and tightening ring.
Figure 20B:
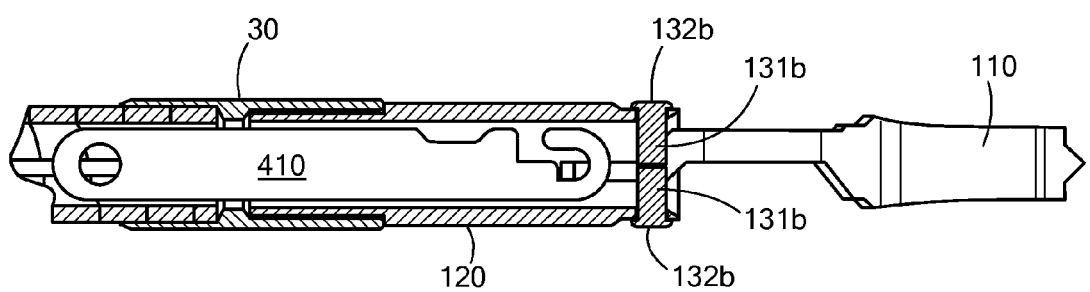
FIG. 20B is a cross sectional view of FIG. 20A in an assembled condition.
Figure 21:
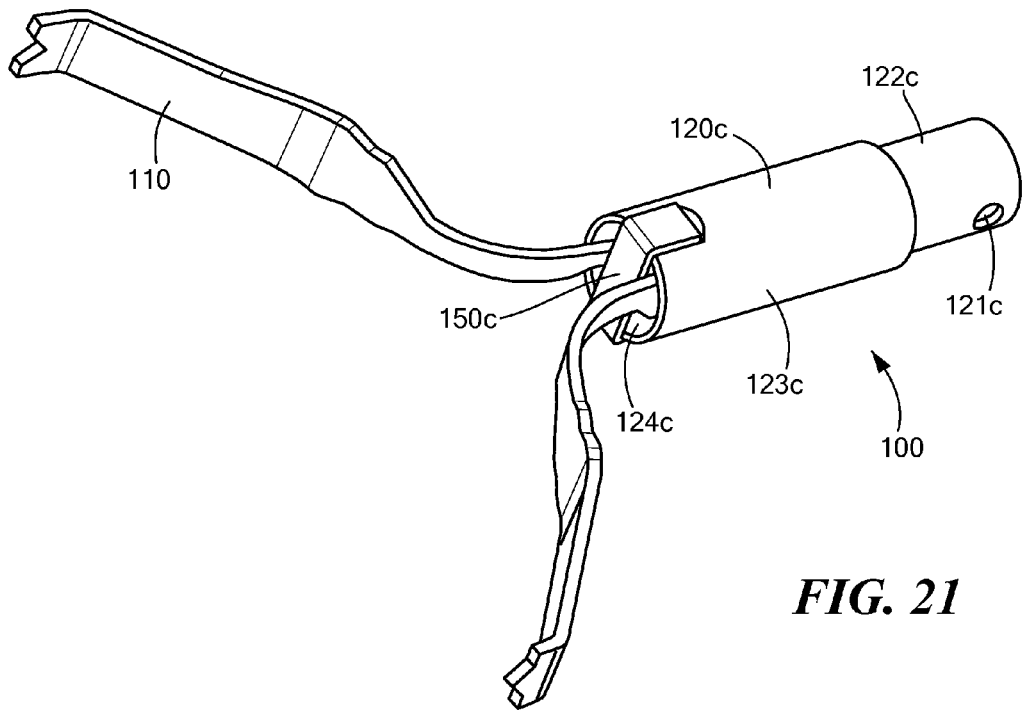
FIG. 21 is an isometric view of a still further embodiment of a clip unit.
Figure 22:
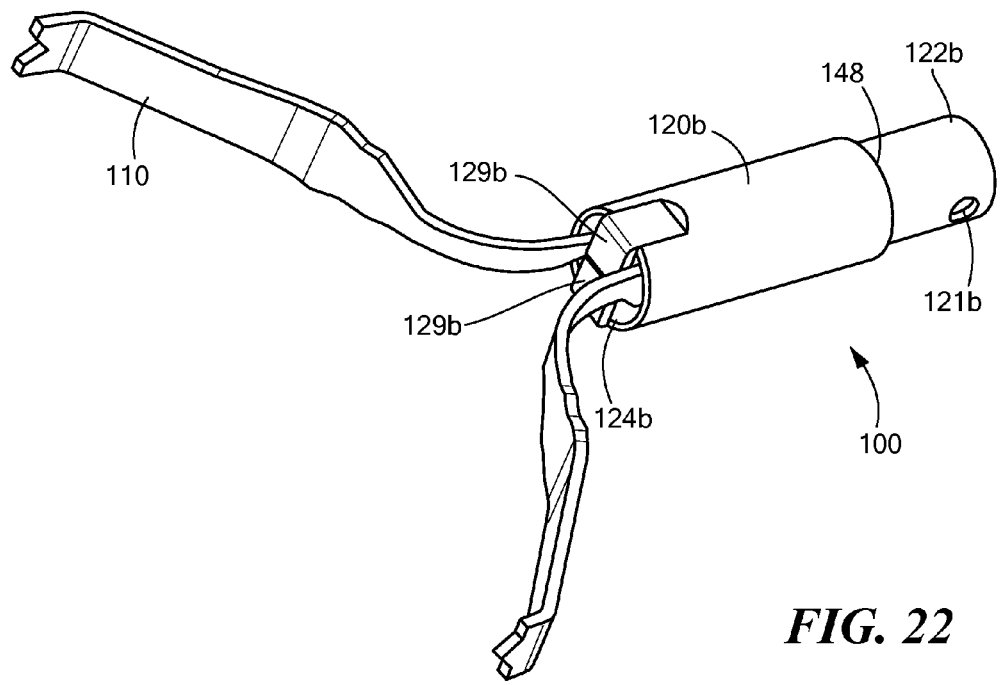
FIG. 22 is an isometric view of a still further embodiment of a clip unit.

Alternative embodiments of a spacer member are illustrated in FIGS. 20A, 20B, 21, and 22. In FIGS. 20A-B, the spacer member 130b is formed of two pin pieces 131b that fit through apertures in the tightening ring 120. The pin pieces include heads 132b that fit within recessed sections surrounding the apertures. The pin pieces can be fastened together within the tightening ring in any suitable manner, such as by welding, adhesive, or the like. Alternatively, the heads of the pin pieces can be fastened to the exterior of the tightening ring in any suitable manner, such as by welding, adhesive, or the like. In FIG. 21, the spacer member is formed from a strip 150c of metal that fits across the distal opening 124c of the tightening ring 120c. Ends of the strip are bent to fit within opposed recesses formed on the exterior of the tightening ring. The ends can be fastened within the recess in any suitable manner, such as by welding, adhesive, or the like. In FIG. 22, two strips 129b are formed and fastened within recesses of the tightening ring in any suitable manner, such as by welding, adhesive, or the like. The strips are bent radially inwardly to extend across the opening 124b.

Figure 23:
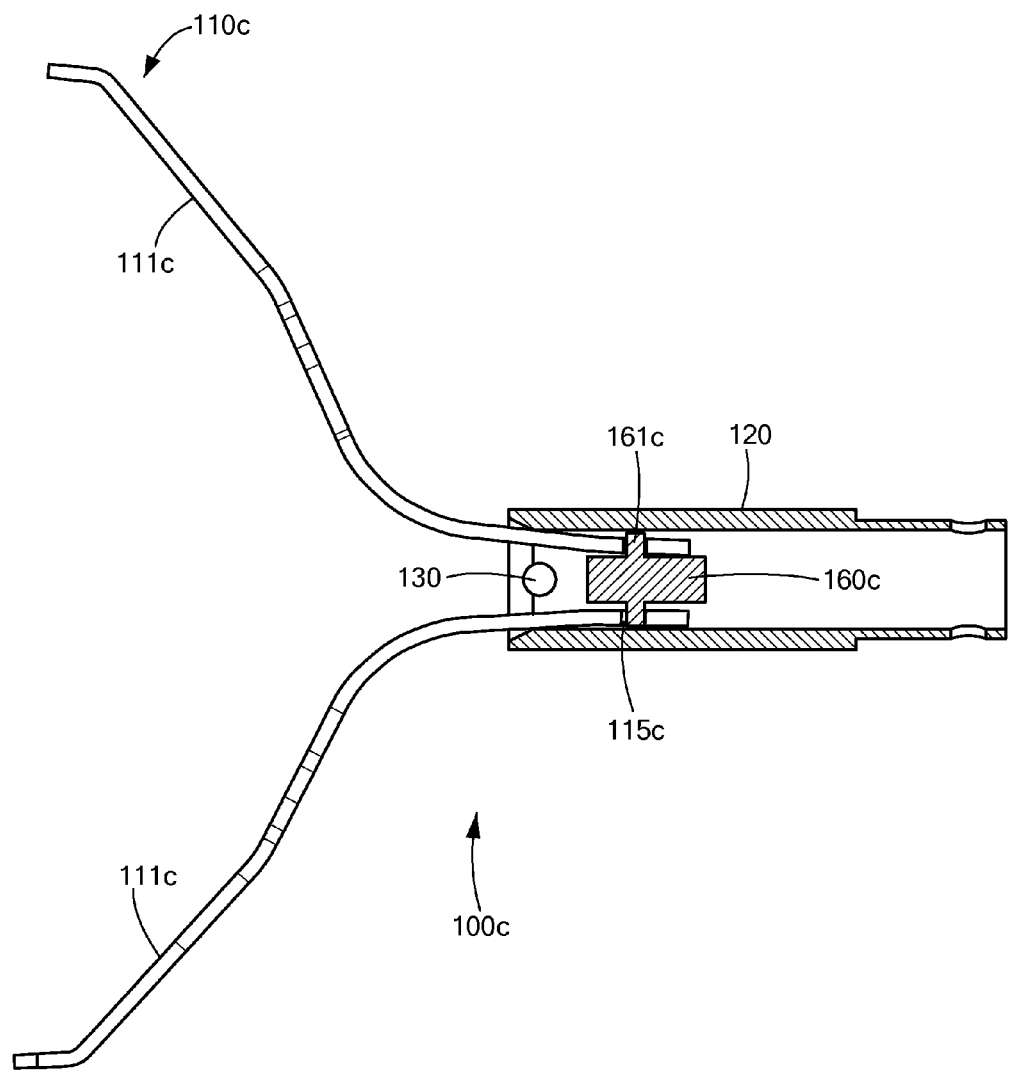
FIG. 23 is a cross sectional view of a further embodiment of a clip unit.
Figure 24:
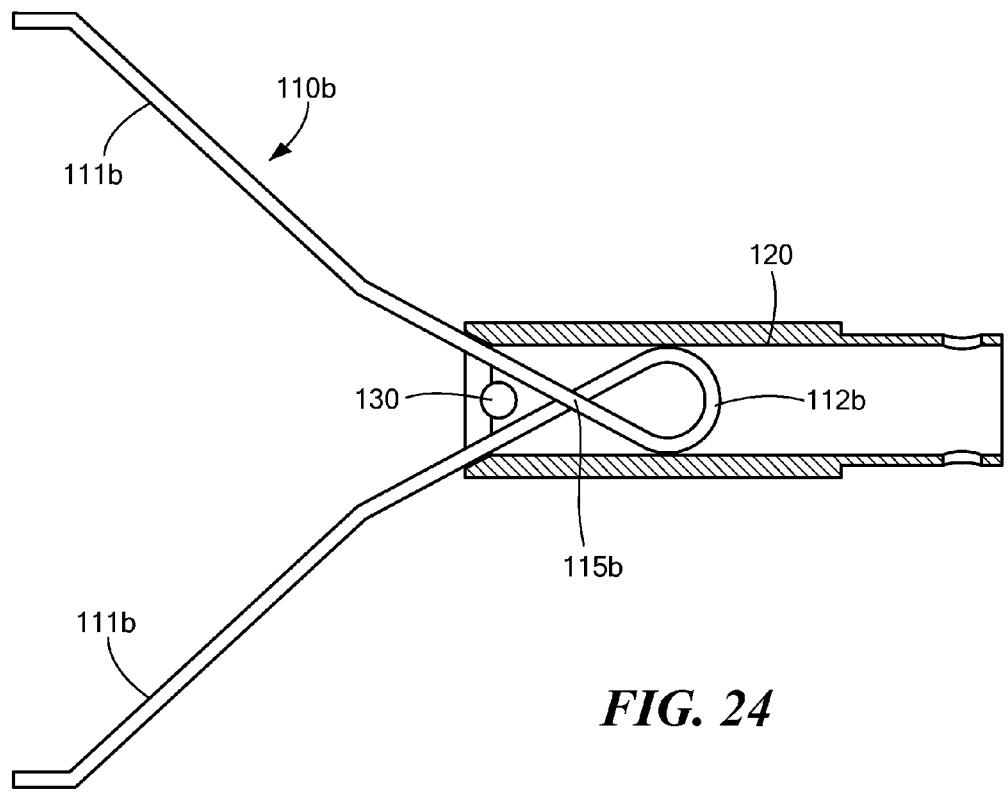
FIG. 24 is a cross sectional view of a still further embodiment of a clip unit.

Alternative embodiments of a clip unit are illustrated in FIGS. 23 and 24. In FIG. 23, the clip 110c includes two arms or strips 111c that are biased outwardly and are fastened by a member 160c at their proximal ends. Member 160c includes tabs 161c that fit within recesses 115c on each arm 111c. Member 160c can be releasably affixed to coupling plate 410 (not shown in FIG. 23) in any suitable manner. The arms or strips 111c can be attached at their proximal ends in any other suitable manner. In FIG. 24, the clip 110b includes two arms 111b that are biased outwardly. The arms are joined at a proximal base 112b and suitably configured to cross at 115b.

Figure 25:
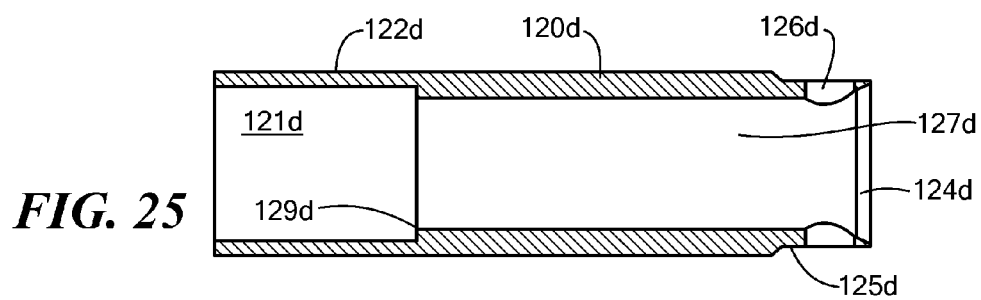
FIG. 25 is a cross sectional view of a further embodiment of a tightening ring.
Figure 26:
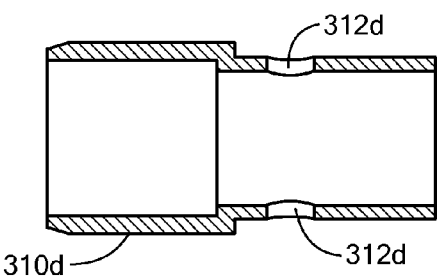
FIG. 26 is a cross sectional view of a further embodiment of a coupling ring.
Figure 27A:
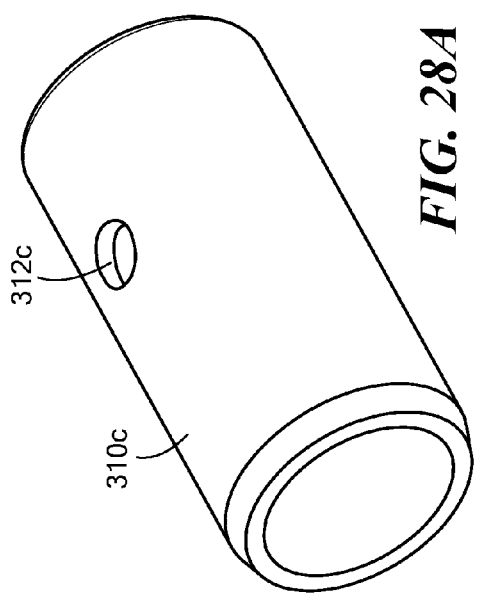
FIG. 27A is an isometric view of a further embodiment of a coupling ring.
Figure 28A:
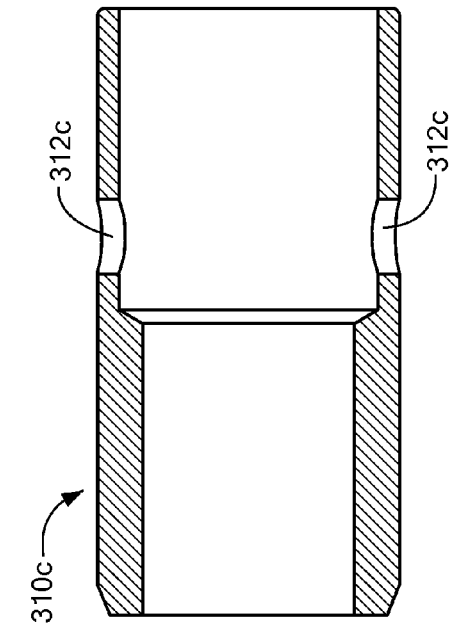
FIG. 28A is an isometric view of a further embodiment of a coupling ring.
Figure 27B:
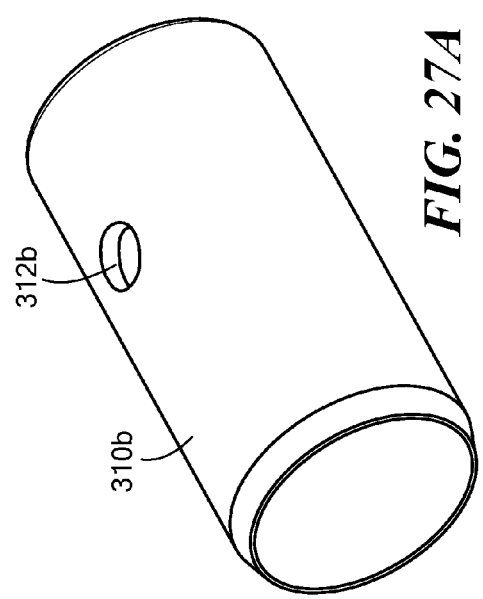
FIG. 27B is a cross sectional view of the coupling ring of FIG. 27A.
Figure 28B:
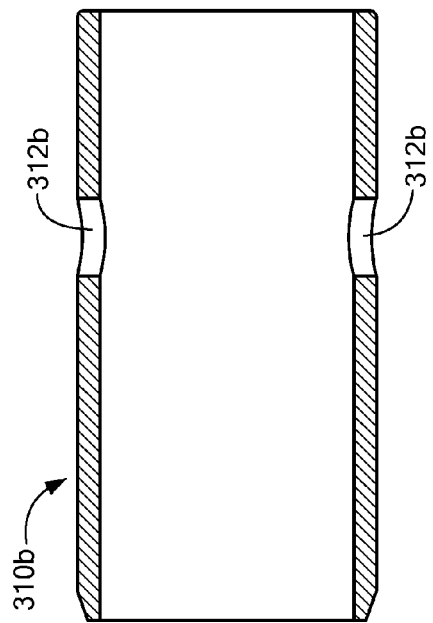
FIG. 28B is a cross sectional view of the coupling ring of FIG. 28A.
Figure 29:
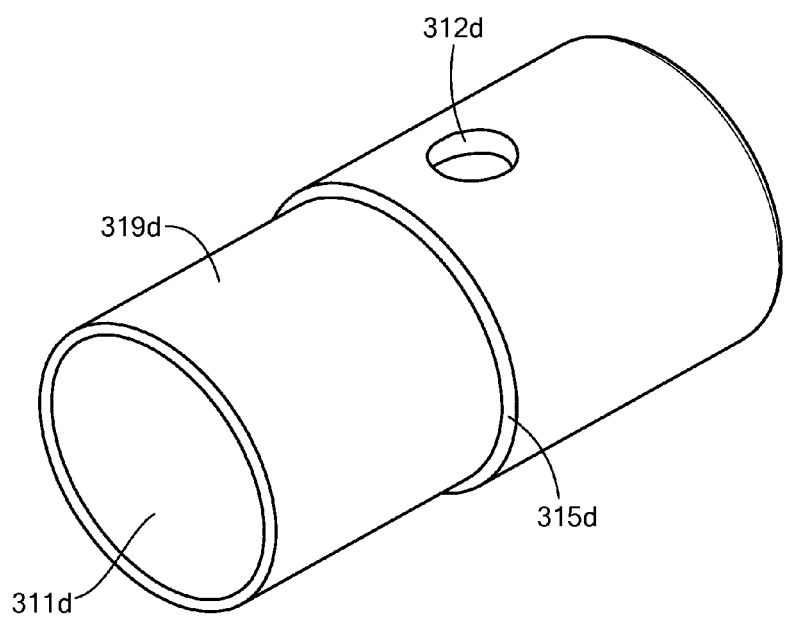
FIG. 29 is an isometric view of a still further embodiment of a coupling ring.

An alternative embodiment of a tightening ring 120d is illustrated in FIG. 25. The tightening ring includes a proximal section 122d having a widened internal diameter to receive a reduced diameter section of a coupling ring (not shown in FIG. 25). The coupling ring may abut a shoulder 129d within the tightening ring 120d. Apertures 121d are provided as described above for receiving a release mechanism. FIG. 26 illustrates a coupling ring 310d having a distal section 313d with a reduced outer diameter that fits within the inner diameter proximal section 122d of the tightening ring 120d. Apertures 312d align with apertures 121d for receiving a release mechanism. Further coupling ring configurations are illustrated in FIGS. 27A and 27B, 28A and 28B, and 29.

FIGS. 30, 30A, 31, 31A, 32, and 32A illustrate further embodiments of a control wire and coupling plate. In FIGS. 30 and 30A, the control wire 420 includes a lengthened wire portion 421 that terminates with a distal wire portion 422 having a widened or oval cross section. The distal portion 422 is attached to the coupling plate 410 in any suitable manner, such as by welding. In FIGS. 31 and 31A, the control wire 420b includes a lengthened wire portion 421b, having a circular cross section of diameter D, that terminates with a tapered portion 423b and a narrowed distal wire portion 422b, having a circular cross section of diameter d. The narrowed distal wire portion 422b is attached to the coupling plate 410 in any suitable manner, such as by welding. In FIGS. 32 and 32A, the control wire 420c has a constant diameter d along its length. A distal portion 420c is attached to the coupling plate 410 in any suitable manner, such as by welding.

Figure 35:
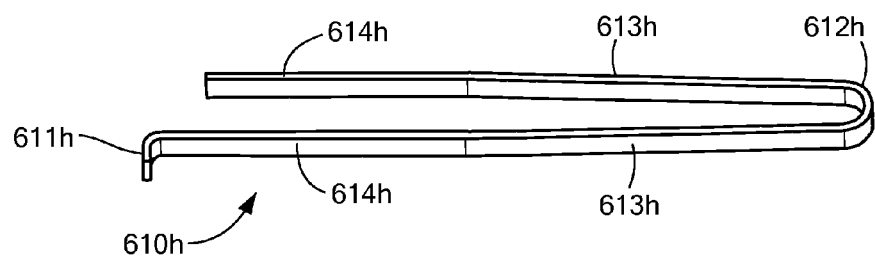
FIG. 35 is an isometric view of a further embodiment of a spring clip.
Figure 36:
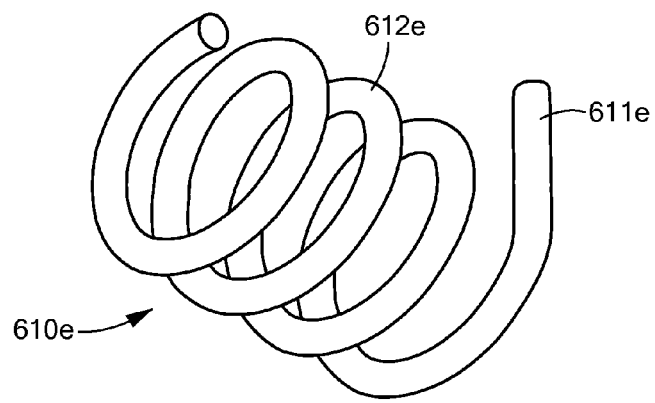
FIG. 36 is an isometric view of a still further embodiment of a spring clip.
Figure 37:
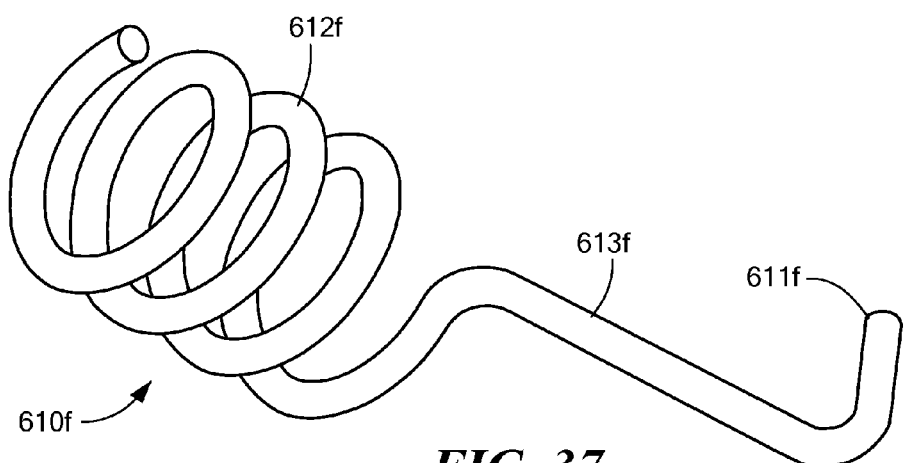
FIG. 37 is an isometric view of a still further embodiment of a spring clip.

Alternative embodiments of the spring pin are illustrated in FIGS. 33, 34, 35, 36, and 37. In FIG. 33, the spring pin 610b has a rectangular cross section. FIGS. 34 and 35 illustrate spring pin 610d, 610h respectively with a single distal tip 611d, 611h that faces outwardly. FIG. 36 illustrates a spring pin 610e having a coil spring configuration 612e with a distal tip 611e. FIG. 37 illustrates a further spring pin 610f with distal tip 611f and an elongated arm portion 613f.

As set forth above, it will be appreciated that the various features and aspects of the several embodiments can be used interchangeably in embodiments other than the particular embodiment in which a particular feature or aspect is illustrated, as would be apparent to one of skill in the art. The invention is not to be limited by what has been particularly shown and described, except as indicated by the appended claims.

What is claimed is:

1. A clip apparatus for the ligature of living tissue, comprising:
- a clip unit comprising a clip, a tightening ring, and a spacer member disposed at a distal end of the tightening ring, the clip having a pair of arms biased outwardly by the spacer member, the clip slidably movable within the tightening ring, the tightening ring configured to close the arms together against the bias, whereby tissue can be clamped between distal jaw ends of the arms;
- a coupling mechanism removably attached to the clip unit, comprising a control wire removably attached at a distal end to the clip unit;
- a handle operation unit, the control wire attached to the handle operation unit for distal and proximal reciprocating movement;
- an introducing mechanism comprising a tube attached at a proximal end to the handle operation unit, and a coupling ring attached to the tube at a distal end of the tube;
- a release mechanism releasably coupling the tightening ring of the clip unit to the coupling ring at the distal end of the tube of the introducing mechanism for coupled proximal and distal movement and including a spring pin removably attached to the tightening ring and the coupling ring; and
- an outer sheath, wherein the clip unit, the coupling mechanism, the introducing mechanism, and the release mechanism are sized and disposed to reciprocate in distal and proximal directions within the outer sheath.

2. The apparatus of claim 1, wherein the spring pin comprises a proximal base and two arms, distal tips of the arms removably attachable to the tightening ring and the coupling ring.

3. The apparatus of claim 1, wherein the coupling mechanism abuts the proximal base of the spring pin upon movement in a proximal direction to detach the spring pin from the tightening ring and the coupling ring, thereby detaching the clip unit.

* * * * *